US009801936B2

(12) United States Patent
Tian et al.

(10) Patent No.: US 9,801,936 B2
(45) Date of Patent: *Oct. 31, 2017

(54) METHOD OF ATTENUATING PORCINE PSEUDORABIES VIRUS, ATTENUATED STRAINS OF PORCINE PSEUDORABIES VIRUS, VACCINE COMPOSITION AND USE THEREOF

(71) Applicant: Pulike Biological Engineering, Inc., Luoyang, Henan (CN)

(72) Inventors: Kegong Tian, Luoyang (CN); Feifei Tan, Luoyang (CN); Jinzhong Sun, Luoyang (CN); Xuke Zhang, Luoyang (CN)

(73) Assignee: PULIKE BIOLOGICAL ENGINEERING, INC., Luoyang, Henan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/213,711

(22) Filed: Jul. 19, 2016

(65) Prior Publication Data

US 2016/0317651 A1 Nov. 3, 2016

Related U.S. Application Data

(63) Continuation of application No. 15/030,345, filed as application No. PCT/CN2015/083354 on Jul. 6, 2015.

(30) Foreign Application Priority Data

Mar. 20, 2015 (CN) .......................... 2015 1 0124250

(51) Int. Cl.

| | |
|---|---|
| ***A61K 39/00*** | (2006.01) |
| ***C12N 7/00*** | (2006.01) |
| ***A61K 39/245*** | (2006.01) |
| ***C12N 7/08*** | (2006.01) |
| ***A61K 39/12*** | (2006.01) |

(52) U.S. Cl.

CPC ............ *A61K 39/245* (2013.01); *A61K 39/12* (2013.01); *C12N 7/00* (2013.01); *C12N 7/08* (2013.01); *A61K 2039/5254* (2013.01); *C12N 2710/16734* (2013.01); *C12N 2710/16764* (2013.01)

(58) Field of Classification Search

None

See application file for complete search history.

(56) References Cited

U.S. PATENT DOCUMENTS 5,674,500 A * 10/1997 Peeters ................ A61K 39/245 424/199.1
6,217,883 B1 * 4/2001 Allan .................. C07K 14/005 424/199.1

OTHER PUBLICATIONS

Brideau et al., "The Us9 Gene Product of Pseudorabies Virus, an Alphaherpesvirus, Is a Phosphorylated, Tail-Anchored Type II Membrane Protein," Journal of Virology vol. 72, No. 6: 4560-4570 (1998).*
Lomniczi et al., "Deletions in the Genomes of Pseudorabies Virus Vaccine Strains and Existence of Four Isomers of the Genomes," Journal of Virology, vol. 49, No. 3: 970-979 (1984).*
Maresch et al., "Oral immunization of wild boar and domestic pigs with attenuated live vaccine protects against Pseudorabies virus infection," Veterinary Microbiology 151: 20-25 (2012).*
Dong et al., "An Overview of Live Attenuated Recombinant Pseudorabies Viruses for Use as Novel Vaccines," Journal of Immunology Research 2014;2014;824630 (2014).*
Bartha, "Experimental reduction of virulence of Aujesky's disease virus," Mag. allator, Lapja, 16: 42-45 (1961).*
Skoda et al., "Immunization against Aujesky's Disease with Live Vaccine," Acta Virol. 8:1-9 (1964).*

* cited by examiner

*Primary Examiner* — Janet L Andres
*Assistant Examiner* — M. Franco Salvoza
(74) *Attorney, Agent, or Firm* — Fish IP Law, LLC

(57) ABSTRACT

This invention provides a method of attenuating porcine pseudorabies virus, which can effectively and reproducibly attenuate porcine pseudorabies virus. The attenuated strain of porcine pseudorabies virus by use of said method can provide effective immunization for pigs.

5 Claims, No Drawings

SEQUENCE LISTING

```
<160> NUMBER OF SEQ ID NOS: 5

<210> SEQ ID NO 1
<211> LENGTH: 3455
<212> TYPE: DNA
<213> ORGANISM: Unknown
<220> FEATURE:
<223> OTHER INFORMATION: the attenuated PRV HN1201-R strain

<400> SEQUENCE: 1

tcctgatctt cctgggcggg atcgcctgcg tggcccggcg ctgcgcgcgg aatcgcatct      60

accggccgcg acccgggcgc ggatcggcgg tccatgcggc gccccgcgg cgcccgcccc      120

ccaaccccgt cgccggggcg cccgtccccc agcccaagat gacgttggcc gagctgcgcc     180

agaagctcgc caccatcgca gaagaacaat aaaaaggtgg tgtttgcata attttgtggg     240

tggcgtttta tctccgtccg cgccgtttta aacctgggca cccccgcgag tctcgcacac     300

accggggttg agaccatgcg gccctttctg ctgcgcgccg cgcagctcct ggcgctgctg     360

gccctggcgc tctccaccga ggccccgagc ctctccgccg agacgacccc gggccccgtc     420
```

```
accgaggtcc cgagtccctc ggccgaggtc tgggacgacc tctccaccga ggccgacgac    480
gatgacctca acggcgacct cgacggcgac gaccgccgcg cgggcttcgg ctcggccctc    540
gcatccctga gggaggcgcc cccggcccat ctggtgaacg tgtccgaggg cgccaacttc    600
accctcgacg cgcgcggcga cggcgccgtg ctggccggga tctggacgtt cctgcccgtc    660
cgcggctgcg acgccgtgtc ggtgaccacg gtgtgcttcg agaccgcgtg ccacccggac    720
ctggtgctgg gccgcgcctg cgtccccgag gccccggaga tgggcatcgg cgactacctg    780
ccgcccgagg tgccgcggct ccggcgcgag ccgcccatcg tcaccccgga gcggtggtcg    840
ccgcacctga gcgtcctgcg ggccacgccc aacgacacgg gcctctacac gctgcacgac    900
gcctcggggc cgcgggccgt gttctttgtg gcggtgggcg accggccgcc cgcgccggcg    960
gacccggtgg gccccgcgcg ccacgagccc cgcttccacg cgctcggctt ccactcgcag   1020
ctcttctcgc ccggggacac gttcgacctg atgccgcgcg tggtctcgga catgggcgac   1080
tcgcgcgaga actttaccgc cacgctggac tggtactacg cgcgcgcgcc cccgcggtgc   1140
ctgctgtact acgtgtacga gccctgcatc taccacccgc gcgcgcccga gtgcctgcgc   1200
ccggtggacc cggcgtgcag cttcacctcg ccggcgcgcg cgcggctggt ggcgcgccgc   1260
gcgtacgcct cgtgcagccc gctgctcggg gaccggtggc tgaccgcctg ccccttcgac   1320
gccttcggcg aggaggtgca cacgaacgcc accgcggacg agtcggggct gtacgtgctc   1380
gtgatgaccc acaacggcca cgtcgccacc tgggactaca cgctcgtcgc caccgcggcc   1440
gagtacgtca cggtcatcaa ggagctgacg gccccggccc gggccccggg caccccgtgg   1500
ggccccggcg gcggcgacga cgcgatctac gtggacggcg tcacgacgcc ggcgccgccc   1560
gcgcgcccgt ggaacccgta cggccggacg acgcccgggc ggctgtttgt gctggcgctg   1620
ggctccttcg tgatgacgtg cgtcgtcggg ggggccatct ggctctgcgt gctgtgctcc   1680
cggcgccggg cggcctcgcg gccgttccgg gtgccgacgc gggcgcggac gcacatgctc   1740
tctccggtgt acaccagcct gcccacgcac gaggactact acgacggcga cgacgacgac   1800
gacgaggagg cgggcgtcat ccgccggcgg cccgcctccc ccagcggaga cagcggctac   1860
gaggggccgt acgcgagcct ggaccccgag gacgagttca gcagcgacga ggacgacggg   1920
ctgtacgtgc gccccgagga ggcgccccgc tccggcttcg acgtctggtt ccgcgatccg   1980
gagaaaccgg aagtgacgaa tggacccaac tatggcgtga ccgccaaccg cctgttgatg   2040
tcccgccccg cttaaatacc gggagaaccg gtccgcccgc attccgacat gcccggcgcc   2100
gcctccgtcg acatggacac gtttgacccc agcgccccg tcccgacgag cgtctcgaac   2160
ccggccgccg acgtcctgct ggcccccaag ggaccccgct ccccgctgcg cccccaggac   2220
gactcggact gctactacag cgagagcgac aacgagacgc ccagcgagtt cctgcgccgc   2280
gtgggacgcc ggcaggcggc gcgtcggaga cgccgccgct gcctgatggg cgtcgcgatc   2340
agcgccaccg cgctggtcat ctgctcgctg tccgcgctac tcgggggcat cgtcgccagg   2400
cacgtgtagc gagcgagcga gcgaacggga gcgggggccc gcccccatcc gccgcgccca   2460
ggagaggggg gagagagcgg ggggttgggc gcgccacgtg gtgtgggcac ggactcggac   2520
ttgtcacaat aaatgggccc cggcgtgtcc gggcgcacac agcagccttc ctctcctccg   2580
cgtctctgtt ccgcccgtct ctcgccggac tcttcttctc caccgcctcc accgtcgcag   2640
ttgtcgcgag cgcgttcgca ccatgggggt gacggccatc accgtggtca cgctgatgga   2700
cggggccggg cgcatccccg ccttcgtggg cgaggcgcac ccggacctgt ggaaggtgct   2760
```

-continued caccgagtgg tgctacgcgt cgatggtgca gcagcggcgc gccgccgacg agaactcgcc 2820
gcggcagcac gtggtgctgc gctcctcgga gatctccccc ggctcgctgg ccctgctgcc 2880
gcgcgccgtg cgccccgtcg tgcggacgcg gtccgacccc acggcgccgt tctacatcac 2940
caccgagacg cacgagctga cgcggcgccc cccggcggac ggctcgaagc ccggggagcc 3000
cctcaggatc agcccacccc cgcggctgga cacggagtgg tcgtccgtcc tgaacgggat 3060
ccagtacctg aactcggggg cccggggcac ggcccccgtc cacctgtgga tcctgggcgc 3120
cgccgacctc tgcgaccagg tgctcctggc cgcctcccgc agcaccgccg ccggagcctc 3180
ccacgcccag acgggcgcgc gcctgacccg gcgccggccc gggctgacgg acgccgacgc 3240
cctggacgtg atcgtcgccg ggatccaggc gacccgcgcc atgttcgcgc gggtccacaa 3300
ccgctcctgg cgccacgccg gcgagtggac ggaggccctg cactcccaga tcgtgacccg 3360
gggcgacgtg cgccggcgcc gaggcgggcg cggcaacgga cgcgagcgcg ccccgcgatg 3420
taccatctcc tagacggcag gatctctccg cgtcc 3455

<210> SEQ ID NO 2
<211> LENGTH: 69
<212> TYPE: PRT
<213> ORGANISM: Unknown
<220> FEATURE:
<223> OTHER INFORMATION: PRV HN1201 strain

<400> SEQUENCE: 2

Leu Ile Phe Leu Gly Gly Ile Ala Cys Val Ala Arg Arg Cys Ala Arg
1 5 10 15

Asn Arg Ile Tyr Arg Pro Arg Pro Gly Arg Gly Ser Ala Val His Ala
20 25 30

Ala Pro Pro Arg Arg Pro Pro Pro Asn Pro Val Ala Gly Ala Pro Val
35 40 45

Pro Gln Pro Lys Met Thr Leu Ala Glu Leu Arg Gln Lys Leu Ala Thr
50 55 60

Ile Ala Glu Glu Gln
65

<210> SEQ ID NO 3
<211> LENGTH: 579
<212> TYPE: PRT
<213> ORGANISM: Unknown
<220> FEATURE:
<223> OTHER INFORMATION: PRV HN1201 strain

<400> SEQUENCE: 3

Met Arg Pro Phe Leu Leu Arg Ala Ala Gln Leu Leu Ala Leu Leu Ala
1 5 10 15

Leu Ala Leu Ser Thr Glu Ala Pro Ser Leu Ser Ala Glu Thr Thr Pro
20 25 30

Gly Pro Val Thr Glu Val Pro Ser Pro Ser Ala Glu Val Trp Asp Asp
35 40 45

Leu Ser Thr Glu Ala Asp Asp Asp Asp Leu Asn Gly Asp Leu Asp Gly
50 55 60

Asp Asp Arg Arg Ala Gly Phe Gly Ser Ala Leu Ala Ser Leu Arg Glu
65 70 75 80

Ala Pro Pro Ala His Leu Val Asn Val Ser Glu Gly Ala Asn Phe Thr
85 90 95

Leu Asp Ala Arg Gly Asp Gly Ala Val Leu Ala Gly Ile Trp Thr Phe
100 105 110

```
Leu Pro Val Arg Gly Cys Asp Ala Val Ser Val Thr Thr Val Cys Phe
        115                 120                 125

Glu Thr Ala Cys His Pro Asp Leu Val Leu Gly Arg Ala Cys Val Pro
    130                 135                 140

Glu Ala Pro Glu Met Gly Ile Gly Asp Tyr Leu Pro Pro Glu Val Pro
145                 150                 155                 160

Arg Leu Arg Arg Glu Pro Pro Ile Val Thr Pro Glu Arg Trp Ser Pro
                165                 170                 175

His Leu Ser Val Leu Arg Ala Thr Pro Asn Asp Thr Gly Leu Tyr Thr
            180                 185                 190

Leu His Asp Ala Ser Gly Pro Arg Ala Val Phe Phe Val Ala Val Gly
        195                 200                 205

Asp Arg Pro Pro Ala Pro Ala Asp Pro Val Gly Pro Ala Arg His Glu
    210                 215                 220

Pro Arg Phe His Ala Leu Gly Phe His Ser Gln Leu Phe Ser Pro Gly
225                 230                 235                 240

Asp Thr Phe Asp Leu Met Pro Arg Val Val Ser Asp Met Gly Asp Ser
                245                 250                 255

Arg Glu Asn Phe Thr Ala Thr Leu Asp Trp Tyr Tyr Ala Arg Ala Pro
            260                 265                 270

Pro Arg Cys Leu Leu Tyr Tyr Val Tyr Glu Pro Cys Ile Tyr His Pro
        275                 280                 285

Arg Ala Pro Glu Cys Leu Arg Pro Val Asp Pro Ala Cys Ser Phe Thr
    290                 295                 300

Ser Pro Ala Arg Ala Arg Leu Val Ala Arg Arg Ala Tyr Ala Ser Cys
305                 310                 315                 320

Ser Pro Leu Leu Gly Asp Arg Trp Leu Thr Ala Cys Pro Phe Asp Ala
                325                 330                 335

Phe Gly Glu Glu Val His Thr Asn Ala Thr Ala Asp Glu Ser Gly Leu
            340                 345                 350

Tyr Val Leu Val Met Thr His Asn Gly His Val Ala Thr Trp Asp Tyr
        355                 360                 365

Thr Leu Val Ala Thr Ala Ala Glu Tyr Val Thr Val Ile Lys Glu Leu
    370                 375                 380

Thr Ala Pro Ala Arg Ala Pro Gly Thr Pro Trp Gly Pro Gly Gly Gly
385                 390                 395                 400

Asp Asp Ala Ile Tyr Val Asp Gly Val Thr Thr Pro Ala Pro Pro Ala
                405                 410                 415

Arg Pro Trp Asn Pro Tyr Gly Arg Thr Thr Pro Gly Arg Leu Phe Val
            420                 425                 430

Leu Ala Leu Gly Ser Phe Val Met Thr Cys Val Val Gly Gly Ala Ile
        435                 440                 445

Trp Leu Cys Val Leu Cys Ser Arg Arg Arg Ala Ala Ser Arg Pro Phe
    450                 455                 460

Arg Val Pro Thr Arg Ala Arg Thr His Met Leu Ser Pro Val Tyr Thr
465                 470                 475                 480

Ser Leu Pro Thr His Glu Asp Tyr Tyr Asp Gly Asp Asp Asp Asp Asp
                485                 490                 495

Glu Glu Ala Gly Val Ile Arg Arg Arg Pro Ala Ser Pro Ser Gly Asp
            500                 505                 510

Ser Gly Tyr Glu Gly Pro Tyr Ala Ser Leu Asp Pro Glu Asp Glu Phe
        515                 520                 525
```

```
Ser Ser Asp Glu Asp Asp Gly Leu Tyr Val Arg Pro Glu Glu Ala Pro
    530                 535                 540

Arg Ser Gly Phe Asp Val Trp Phe Arg Asp Pro Glu Lys Pro Glu Val
545                 550                 555                 560

Thr Asn Gly Pro Asn Tyr Gly Val Thr Ala Asn Arg Leu Leu Met Ser
                565                 570                 575

Arg Pro Ala


<210> SEQ ID NO 4
<211> LENGTH: 98
<212> TYPE: PRT
<213> ORGANISM: Unknown
<220> FEATURE:
<223> OTHER INFORMATION: PRV HN1201 strain

<400> SEQUENCE: 4

Met Asp Thr Phe Asp Pro Ser Ala Pro Val Pro Thr Ser Val Ser Asn
1               5                   10                  15

Pro Ala Ala Asp Val Leu Leu Ala Pro Lys Gly Pro Arg Ser Pro Leu
            20                  25                  30

Arg Pro Gln Asp Asp Ser Asp Cys Tyr Tyr Ser Glu Ser Asp Asn Glu
        35                  40                  45

Thr Pro Ser Glu Phe Leu Arg Arg Val Gly Arg Arg Gln Ala Ala Arg
    50                  55                  60

Arg Arg Arg Arg Arg Cys Leu Met Gly Val Ala Ile Ser Ala Thr Ala
65                  70                  75                  80

Leu Val Ile Cys Ser Leu Ser Ala Leu Leu Gly Gly Ile Val Ala Arg
                85                  90                  95

His Val


<210> SEQ ID NO 5
<211> LENGTH: 255
<212> TYPE: PRT
<213> ORGANISM: Unknown
<220> FEATURE:
<223> OTHER INFORMATION: PRV HN1201 strain

<400> SEQUENCE: 5

Met Gly Val Thr Ala Ile Thr Val Val Thr Leu Met Asp Gly Ala Gly
1               5                   10                  15

Arg Ile Pro Ala Phe Val Gly Glu Ala His Pro Asp Leu Trp Lys Val
            20                  25                  30

Leu Thr Glu Trp Cys Tyr Ala Ser Met Val Gln Gln Arg Arg Ala Ala
        35                  40                  45

Asp Glu Asn Ser Pro Arg Gln His Val Val Leu Arg Ser Ser Glu Ile
    50                  55                  60

Ser Pro Gly Ser Leu Ala Leu Leu Pro Arg Ala Val Arg Pro Val Val
65                  70                  75                  80

Arg Thr Arg Ser Asp Pro Thr Ala Pro Phe Tyr Ile Thr Thr Glu Thr
                85                  90                  95

His Glu Leu Thr Arg Arg Pro Pro Ala Asp Gly Ser Lys Pro Gly Glu
            100                 105                 110

Pro Leu Arg Ile Ser Pro Pro Pro Arg Leu Asp Thr Glu Trp Ser Ser
        115                 120                 125

Val Leu Asn Gly Ile Gln Tyr Leu Asn Ser Gly Ala Arg Gly Thr Ala
    130                 135                 140

Pro Val His Leu Trp Ile Leu Gly Ala Ala Asp Leu Cys Asp Gln Val
```

-continued

```
145                 150                 155                 160

Leu Leu Ala Ala Ser Arg Ser Thr Ala Ala Gly Ala Ser His Ala Gln
                165                 170                 175

Thr Gly Ala Arg Leu Thr Arg Arg Arg Pro Gly Leu Thr Asp Ala Asp
            180                 185                 190

Ala Leu Asp Val Ile Val Ala Gly Ile Gln Ala Thr Arg Ala Met Phe
        195                 200                 205

Ala Arg Val His Asn Arg Ser Trp Arg His Ala Gly Glu Trp Thr Glu
    210                 215                 220

Ala Leu His Ser Gln Ile Val Thr Arg Gly Asp Val Arg Arg Arg Arg
225                 230                 235                 240

Gly Gly Arg Gly Asn Gly Arg Glu Arg Ala Pro Arg Cys Thr Ile
                245                 250                 255
```

METHOD OF ATTENUATING PORCINE PSEUDORABIES VIRUS, ATTENUATED STRAINS OF PORCINE PSEUDORABIES VIRUS, VACCINE COMPOSITION AND USE THEREOF

This application is a continuation of U.S. patent application Ser. No. 15/030,345, filed Apr. 18, 2016, which is a U.S. National Phase of PCT/CN2015/083354, filed Jul. 6, 2015, and claims the benefit of priority to Chinese Patent Application No. 201510124250.0, filed Mar. 20, 2015.

FIELD OF THE INVENTION

This invention relates to a method of attenuating porcine pseudorabies virus, attenuated strains of porcine pseudorabies virus and vaccine composition prepared therefrom, belonging to the field of veterinary biological products.

BACKGROUND OF THE INVENTION

Pseudorabies, also called Aujeszky's disease, is an acute infectious disease caused by Suid herpesvirus 1 (SuHV1) belonging to the Alphaherpesvirinae subfamily for many kinds of livestock such as swine, cattle and sheep, as well as poultry and wild animals, with the main symptoms of fever, intense itching (except swine) and encephalomyelitis. Pseudorabies in swine is found nationwide in China causing severe damages, and is one of the major diseases limiting the large-scale production of pig farms. It can result in abortion, stillborn or mummified fetuses in pregnant sows, and neurological signs, paralysis and a high death rate in piglets. Pseudorabies virus (PRV) with strong pantropic properties, neurotropic properties and latent infectivity, may establish long-term latent infection in the peripheral nervous system, and then the latently infected host starts to get sick when the latent virus is activated into the infectious virus.

According to recent research, there are reports of new features of pseudorabies, of which the significant manifestations include infection among swine at any age, horizontal transmission among swine herds, short incubation period (1~2 days), morbidity rates between 10%~100%, mortality rate in pigs between 10%~100% (mortality rate in piglets can reach up to 100%), high fever in pigs after being infected (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their forelimbs, and finally dying of exhaustion, and the infection also can cause reproductive disorder symptoms such as declined semen quality of boar, as well as abortion of pregnant sow (the abortion rate can reach up to 35%), premature birth, stillbirth, weakened piglets (weakened piglets die by 14 days of age), etc. Vaccinated pigs in prior art cannot complete resist attacks by the wild virus, and still have symptoms like high fever, depression, partially or completely loss of appetite, with an infection rate of more than 80%, a morbidity rate of more than 30% and a mortality rate between 10% and 20% (Refer to literatures in the prior art, for example, Jin-mei Peng, et al., Identification and antigenic variation of new epidemiology of pseudorabies virus from swine. Chinese Journal of Preventive Veterinary Medicine, 2013, 35(1):1-4; Wu Tong et al., Identification and Characterization of a pseudorabies virus isolated from a dead piglet born to vaccinated sow. Chinese Journal of Animal infectious diseases, 2013, 21(3):1-7; Yu et al., Pathogenic Pseudorabies Virus, China, 2012. Emerging infectious Diseases. 2014, 20(1):102-104; An et al., Pseudorabies virus variant in Bartha-K61-vaccinated pigs, China, Emerging infectious Diseases. 2013. 19(11): 1749-1755. There are no vaccines capable of solving the pseudorabies caused by variant strains of porcine pseudorabies virus in the prior art.

An effective method of preventing and controlling the pseudorabies caused by variant strains of porcine pseudorabies virus is inoculation with vaccines. The commercial vaccines to be developed may be inactivated vaccines, and also live vaccines prepared from attenuated strains. However, the cost of inactivated vaccines is relatively high, and usually the live vaccines are prepared by attenuating the strain via a deficiency of virulent genes by means of genetic engineering, resulting in the biosafety risk.

SUMMARY OF INVENTION

In order to solve the above problems, in the present invention strains are attenuated naturally by means of cell passage, so that they can have genetic variation during the natural evolutionary process, in order to completely adapt to natural environments and conditions, and ensure stability of the attenuated strains, without any biosafety risk.

The first aspect of the present invention relates to a method of attenuating porcine pseudorabies virus, comprising: (1) a step of cultivating the pseudorabies virus adapted to cell culture, wherein the pseudorabies virus is inoculated into subcultured mammalian cells, and then subcultured for at least five passages so as to obtain the pseudorabies virus strain adapted to subcultured mammalian cells; (2) a step of attenuating the pseudorabies virus, wherein the pseudorabies virus strain adapted to subcultured mammalian cells is inoculated into subcultured avian cells and then subcultured for at least one passage so as to obtain the attenuated strain of pseudorabies virus.

As an embodiment of the present invention, in said method of attenuating the pseudorabies virus according to the present invention, said pseudorabies virus in step (1) comprises PRV JS-2012 strain, PRV HeN1 strain, NVDC-PRV-BJ strain, NVDC-PRV-HEB strain and NVDC-PRV-SD strain, PRV TJ strain, PRV variant strain PRV-ZJ01, PRV variant strain HN1201, PRV variant strain HN1202 and PRV Fa strain.

PRV JS-2012 strain has been disclosed in Isolation and identification of PRV from piglets infected after immunization [J]. Wu Tong, Qingzhan Zhang, Hao Zheng et al. Chinese Journal of Animal Infectious Diseases. 2013, 21(3): 1-7; PRV HeN1 strain is deposited in the China General Microbiological Culture Collection Center with the accession number CGMCC NO. 6656 and has been disclosed in the patent application CN102994458A; NVDC-PRV-BJ strain, NVDC-PRV-HEB strain and NVDC-PRV-SD strain have been disclosed in the literature, Pathogenic Pseudorabies Virus, Xiuling Yu, Zhi Zhou, Dongmei Hu, et al. China, 2012 Emerging Infectious Diseases, No. 1, January 2014; PRV TJ strain has been disclosed in the literature, a novel gE-deleted pseudorabies virus (PRV) provides rapid and complete protection from lethal challenge with the PRV variant emerging in Bartha-K61-vaccinated swine population in China. Chun-Hua Wang Jin Yuan, Hua-Yang Qin, et al, Vaccine. 32 (2014) 3379-3385; PRV variant strain PRV-ZJ01 has been disclosed in CN103627678A with the accession number, CGMCC No. 8170; HN1201 strain (pseudorabies virus, strain HN1201) has been deposited in the China Center for Type Culture Collection on May 20, 2013, of which the accession number is CCTCC NO. V 201311 and the address of depositary is Wuhan University, Wuhan, China; PRV HN1202 strain (pseudorabies virus, strain HN1202) has been deposited in the China Center for Type Culture Collection on Aug. 26, 2013, of which the accession number is CCTCC NO. V 201335 and the address of depositary is Wuhan University, Wuhan, China; PRV Fa strain has been disclosed in Cloning and Sequence analysis of gB, gC, gD genes of pseudorabies virus strain Fa [J]. Zheng-hai Chen, et al. Fujian Journal of Agricultural Sciences.

As a preferred embodiment of the present invention, said porcine pseudorabies virus in step (1) comprises HN1201 strain, HN1202 strain, Fa strain, PRV-ZJ01 strain, HeN1 strain, and JS-2012 strain.

As an embodiment of the present invention, in said method of attenuating the pseudorabies virus according to the present invention, said subcultured mammalian cells in the step (1) comprise swine testicle cell line ST, subcultured swine kidney cell line PK-15 or MRS-2, subcultured rabbit kidney cell line RK, subcultured African green monkey kidney cell line vero, subcultured monkey embryonic kidney epithelial cell line Marc-145, subcultured bovine testicle cell line BT or subcultured Syrian baby hamster kidney cell line BHK-21; said avian subcultured cell line in the step (2) are DF-1.

Said subcultured mammalian cells are subcultured swine testicle cell line ST (ATCC CRL-1746), subcultured swine kidney cell line PK-15 (ATCC CCL-33) or MRS-2 (refer to, e.g. DECASTRO, M. P. 1964. Behavior of foot and mouth disease virus in cell culture: susceptibility of the IB-RS-2 swine cell line. Arquivos Instituto Biologica 31: 63-78), subcultured rabbit kidney cell line RK(ATCC CCL-106), subcultured African green monkey kidney cell line vero (ATCC CCL-81), subcultured monkey embryonic kidney epithelial cell line Marc-145 (ATCC CRL-12219), subcultured bovine kidney cell line MDBK (ATCC CCL-22), subcultured bovine testicle cell line BT (ATCC CRL-1390), and subcultured baby hamster kidney cell line BHK-21 (ATCC CCL-10).

As a preferred embodiment of the present invention, said subcultured mammalian cells in the step (1) is subcultured swine testicle cells ST, subcultured swine kidney cells PK-15 or subcultured monkey embryonic kidney epithelial cells Marc-145; preferably, said avian subcultured cells in the step (2) are DF-1(ATCC CRL-12203).

As an embodiment of the present invention, in said method of attenuating the pseudorabies virus according to the present invention, said step of cultivating the pseudorabies virus adapted to cell culture in the step (1) comprises:

Said subcultured mammalian cells being dispersed and digested with trypsin, and continued to be cultured with cell growth medium, forming a monolayer of subcultured cells; and said pseudorabies virus being inoculated into said monolayer of subcultured cells and continued to be cultured with cell growth medium; after 40 h~48 h, the cell medium containing viruses being harvested as the virus seed for continuous passages when the cytopathic effect of cells reached 80%, said passage continuing to at least 5 passages, so as to obtain the pseudorabies virus strain adapted to subcultured mammalian cells. Preferably, the passage number of the pseudorabies virus strain in the mammalian cells in the step (1) is at least 5.

Preferably, the passage number of the pseudorabies virus strain in the mammalian cells in the step (1) is equal to or at least 18.

Preferably, the Step (1) further comprises the following steps:

(1a) Subculture and cultivation of cells for inoculation of virus: said subcultured cells are dispersed and digested with trypsin, and continued to be cultured with cell growth medium, forming a monolayer of subcultured cells;

(1b) proliferation of virus: said pseudorabies virus being inoculated into said monolayer of subcultured cells obtained in the step (1a) and continued to be cultured with cell growth medium; after 40 h~48 h, the cell medium containing viruses being harvested as the virus seed for continuous passages when the cytopathic effect of cells reached 80%.

Preferably, the temperature for culturing the cell in the step (1a) and (1b) is within the range of 36° C.~38° C.

Preferably, the pseudorabies virus for inoculation in the step (1b) is 1%~2% (v/v) PRV maintenance medium.

Preferably, the cell growth medium in the step (1a) comprises 90%~97% (V/V) cell culture medium and 3%~10% (V/V) bovine serum, and the pH value of said cell growth medium is in the range of 7.0~8.0.

Preferably, the cell maintenance medium in the step (1b) comprises 95%~99% (V/V) cell culture medium and 1%~5% (V/V) bovine serum, and the pH value of the said cell maintenance medium is in the range of 7.1~7.5.

Wherein, said cell culture medium which is suitable for culturing the subcultured cells in which the PRV can reproduce easily, includes, but is not limited to, any one selected from a group consisting of MEM medium, DMEM medium, EMEM medium, 199 medium, 1640 medium and α-MEM medium, and said bovine serum includes but is not limited to fetal calf serum, new-born calf serum or calf serum.

Preferably, said cell culture medium is DMEM medium, and said bovine serum is fetal calf serum.

As an embodiment of the present invention, in said method of attenuating the PRV according to the present invention, wherein, the said step of attenuating the pseudorabies virus in the Step (2) comprises:

Said subcultured avian cells being dispersed and digested with trypsin, and continued to be cultured with cell growth medium, forming a monolayer of subcultured cells; said pseudorabies virus strain adapted to subcultured mammalian cells being inoculated into said monolayer of subcultured avian cells obtained in the step (1) and continued to be cultured with cell maintenance medium; after 40 h~48 h, the cell medium containing viruses, i.e. the attenuated strain of pseudorabies virus, was harvested when the cytopathic effect of cells reached 80%; or the harvested virus solution being subcultured for at least one passage to obtain the attenuated strain of pseudorabies virus.

Preferably, the passage number of the pseudorabies virus strain adapted to subcultured mammalian cells in the subcultured avian cells in step (2) is at least 1.

Preferably, the passage number of the pseudorabies virus strain adapted to subcultured mammalian cells in the subcultured avian cells in step (2) is at least 3.

Preferably, the passage number of the pseudorabies virus strain adapted to subcultured mammalian cells in the subcultured avian cells in step (2) is in the range of 3~110.

Preferably, the Step (2) further comprises the following steps:

(2a) Subculture and cultivation of cells for inoculation of virus: said subcultured cells being dispersed and digested with trypsin, and continued to be cultured with cell growth medium, forming a monolayer of subcultured cells;

(2b) proliferation of virus: said pseudorabies virus obtained in the step (1) being inoculated into said monolayer of subcultured cells obtained in the step (2a) and continued to be cultured with cell maintenance medium; after 40 h~48 h, the cell medium containing viruses, i.e. the attenuated strain of pseudorabies virus, being harvested when the cytopathic effect of cells reaches 80%.

Preferably, the temperature for culturing the cells in the step (2a) and (2b) is within the range of 36° C.~38° C.

Preferably, the pseudorabies virus for inoculation in the step (2b) is 1%~2% (v/v) PRV maintenance medium.

Preferably, the cell growth medium in the step (2a) comprises 90%~97% (V/V) cell culture medium and 3%~10% (V/V) bovine serum, and the pH value of said cell growth medium is in the range of 7.0~8.0.

Preferably, the cell maintenance medium in the step (2b) comprises 95%~99% (V/V) cell culture medium and 1%~5% bovine serum, and the pH value of said cell maintenance medium is in the range of 7.1~7.5.

Wherein, said cell culture medium which is suitable for culturing the subcultured avian cells in which the PRV can reproduce easily includes, but is not limited to, any one selected from a group of MEM medium, DMEM medium, EMEM medium, 199 medium, 1640 medium and α-MEM medium, said bovine serum includes but is not limited to fetal calf serum, new-born calf serum or calf serum.

Preferably, said cell culture medium is DMEM medium, and said bovine serum is fetal calf serum.

As a preferred embodiment of the present invention, in said method of attenuating the pseudorabies virus according to the present invention, the passage number of the pseudorabies virus strain in the mammalian cells in the step (1) is equal to or at least 18; the passage number of the pseudorabies virus strain adapted to the subcultured mammalian cells in the subcultured avian cells in the step (2) is at least 3.

As a preferred embodiment of the present invention, in said method of attenuating the pseudorabies virus according to the present invention, the passage number of the pseudorabies virus strain in the mammalian cells in the step (1) is equal to or at least 18; the passage number of the pseudorabies virus strain adapted to subcultured mammalian cells in the subcultured avian cells in the step (2) is in the range of 3~110.

As a preferred embodiment of the present invention, in said method of attenuating the pseudorabies virus according to the present invention, said cell growth medium comprises 90%~97% (V/V) cell culture medium and 3%~10% bovine serum, and the pH value of said cell growth medium is in the range of 7.0~8.0; said cell maintenance medium comprises 95%~99% (V/V) cell culture medium and 1%~5% bovine serum, and pH value of said cell maintenance medium is in the range of 7.1~7.5; said cell culture medium comprises MEM medium, DMEM medium, EMEM medium, 199 medium, 1640 medium and α-MEM medium, and said bovine serum comprises fetal calf serum, new-born calf serum or calf serum; and the temperature for culturing said cells is within the range of 36° C.~38° C.

As a most preferred embodiment of the present invention, said cell growth medium is DMEM medium, and said bovine serum is fetal calf serum; the temperature for culturing said cells is within the range of 36° C.~38° C.

Another aspect of the invention is to provide attenuated strains of porcine pseudorabies virus by using said method of attenuating the porcine pseudorabies virus, wherein said attenuated strains of porcine pseudorabies virus cannot express gI, gE, 11K or 28K proteins.

Preferably, compared with its parent virulent strain, the genes of said attenuated strains of porcine pseudorabies virus obtained in the Step (2), cannot express gI, gE, 11K or 28K proteins.

Preferably, compared with its parent virulent strain, the genes of said attenuated strains of porcine pseudorabies virus obtained in the Step (2), have a deficiency of gI/gE/11K/28K genes.

As a preferred embodiment of the present invention, in said attenuated strain of porcine pseudorabies virus according to the present invention, the genes of said attenuated strains of porcine pseudorabies virus have continuous deficiency of 3455 bp started from the site of the $890^{th}$ nucleotide of gI gene.

Preferably, said strain of porcine pseudorabies virus is a variant strain of pseudorabies virus, comprising PRV HN1201 strain, PRV HN1202 strain, PRV Fa strain, PRV PRV-ZJ01 strain, PRV HeN1 strain and PRV JS-2012 strain.

Preferably, compared with its parent virulent strain, the genes of said attenuated strain of porcine pseudorabies virus obtained in the Step (2), have continuous deficiency f 3455 bp started from the site of the $890^{th}$ nucleotide of gI gene.

As a most preferred embodiment of the present invention, said attenuated strain of porcine pseudorabies virus is PRV HN1201-R strain (Pseudorabies virus, strain HN1201-R), wherein said PRV HN1201-R strain is deposited in the China Center for Type Culture Collection on Mar. 17, 2015, of which the accession number is CCTCC NO. V201516 and the address of depositary is Wuhan University, Wuhan, China.

As a most preferred embodiment of the present invention, said attenuated strain of porcine pseudorabies virus is PRV HN1202-R strain.

As a most preferred embodiment of the present invention, said attenuated strain of porcine pseudorabies virus is PRV Fa-R strain.

As a most preferred embodiment of the present invention, said attenuated strain of porcine pseudorabies virus is PRV PRV-ZJ01-R strain.

As a most preferred embodiment of the present invention, said attenuated strain of porcine pseudorabies virus is PRV HeN1-R strain.

As a most preferred embodiment of the present invention, said attenuated strain of porcine pseudorabies virus is PRV JS-2012-R strain.

As a preferred embodiment of the present invention, the attenuated strain of PRV HN1201 strain was obtained through the method of attenuating the pseudorabies virus according to the invention, named PRV HN1201-R strain. Compared with PRV HN1201 strain, the genes of PRV HN1201-R strain have continuous deficiency of gI/gE/11K/28K genes (3455 bp in total), of which the deleted sequence is as shown in SEQ No. 1, comprising the amino acid sequence of gI protein as shown in SEQ No. 2, the amino acid sequence of gE protein as shown in SEQ No. 3, the amino acid sequence of 11K protein as shown in SEQ No. 4 and the amino acid sequence of 28K protein as shown in SEQ No. 5.

The pathogenicity test indicated that, the cultures of the $1^{st}$ passage to $110^{th}$ passage of PRV HN1201-R displayed a significant reduction of pathogenicity to pigs. During the observation of piglets for 28 days after inoculation, there were no clinical signs, or no changes in tissues or organs obtained from the necropsy. Therefore, compared with the parent virulent strain, i.e. PRV HN1201 strain, PRV HN1201-R strain displayed a significant reduction of pathogenicity, and was an artificially attenuated virus strain.

According to the immunogenicity assay, it revealed that the culture of the $110^{th}$ passage of PRV HN1201-R strain can still maintain excellent immunogenicity. The piglets, on day 21 after inoculation, can be protected against the virulent strain, PRV HN1201 strain. Meanwhile, the piglets which were not inoculated with the culture of HN1201-R strain, cannot resist the attack from PRV HN1201 strain, and all displayed the disease.

It showed in the reversion of virulence assay that, after inoculation of the cultures of the $1^{st}$ to $110^{th}$ passages of the virus in pig herd, no reversion of virulence of the virus were found during passage of the viruses through continuous contact of pigs. Therefore, safety of the vaccines can be ensured since the virus, after being inoculated into pig herd, would not evolve into a virulent virus which is able to cause disease.

As a preferred embodiment of the present invention, the attenuated strain of PRV HN1202 strain was obtained through the method of attenuating the pseudorabies virus according to the invention, named PRV HN1202-R strain. Compared with PRV HN1202 strain, the genes of PRV HN1202-R strain have continuous deficiency of gI/gE/11K/28K genes (3455 bp in total), in which the site and size of deleted genes are totally the same as those of PRV HN1201-R strain.

The pathogenicity test indicated that, the cultures of the $1^{st}$ passage to $110^{th}$ passage of PRV HN1202-R displayed a significant reduction of pathogenicity in pigs. During the observation of piglets for 28 days after inoculation, there were no clinical signs, or no changes in tissues or organs obtained from the necropsy. Therefore, compared with the parent virulent strain, i.e. PRV HN1202 strain, PRV HN1202-R strain displayed a significant reduction of pathogenicity, and was an artificially attenuated virus strain.

According to the immunogenicity assay, it revealed that the culture of the $110^{th}$ passage of PRV HN1202-R strain can still maintain excellent immunogenicity. The piglets, on day 21 after inoculation, can be protected against the virulent strain, PRV HN1202 strain. Meanwhile, the piglets, which were not inoculated with the culture of HN1202-R strain, cannot resist the attack from PRV HN1202 strain, and all displayed the disease.

It showed in the reversion of virulence assay that, after inoculation of the cultures of the $1^{st}$ to $110^{th}$ passages of the virus in pig herd, no reversion of virulence of the virus was found during passage of the viruses through continuous contact of pigs. Therefore, the safety of the vaccines can be ensured since the virus, after being inoculated into pig herd, would not evolve into a virulent virus which is able to cause disease.

As a preferred embodiment of the present invention, the attenuated strain of PRV Fa strain was obtained through the method of attenuating the pseudorabies virus according to the invention, named PRV Fa-R strain. Compared with PRV Fa strain, the genes of PRV Fa-R strain have continuous deficiency of gI/gE/11K/28K genes (3455 bp in total), in which the site and size of deleted genes are totally the same as those of PRV HN1201-R strain.

The pathogenicity test indicated that the cultures of the $1^{st}$ passage to $110^{th}$ passage of PRV Fa-R displayed a significant reduction of pathogenicity in pigs. During the observation of piglets for 28 days after inoculation, there were no clinical signs, or no changes in tissues or organs obtained from the necropsy. Therefore, compared with the parent virulent strain, i.e. PRV Fa strain, PRV Fa-R strain displayed a significant reduction of pathogenicity, and was an artificially attenuated virus strain.

According to the immunogenicity assay, it revealed that the culture of the $110^{th}$ passage of PRV Fa-R strain can still maintain excellent immunogenicity. The piglets, on day 21 after inoculation, can be protected against the virulent strain, PRV Fa strain. Meanwhile, the piglets, which were not inoculated with the culture of PRV Fa-R strain, cannot resist the attack from PRV Fa strain, and all displayed the disease.

It showed in the reversion of virulence assay that, after inoculation of the cultures of the $1^{st}$ to $110^{th}$ passages of virus in pig herd, no reversion of virulence of the virus was found during passage of the viruses through continuous contact of pigs. Therefore, the safety of the vaccines can be ensured since the virus, after being inoculated into pig herd, would not evolve into a virulent virus which is able to cause disease.

As a preferred embodiment of the present invention, the attenuated strain of PRV PRV-ZJ01 strain was obtained through the method of attenuating the pseudorabies virus according to the invention, named PRV PRV-ZJ01-R strain. Compared with PRV PRV-ZJ01 strain, the genes of PRV PRV-ZJ01-R strain have continuous deficiency of gI/gE/11K/28K genes (3455 bp in total), in which the site and size of deleted genes are totally the same as those of PRV HN1201-R strain.

The pathogenicity test indicated that the cultures of the $1^{st}$ passage to $110^{th}$ passage of PRV PRV-ZJ01-R displayed a significant reduction of pathogenicity to pigs. During the observation of piglets for 28 days after inoculation, there were no clinical signs, or any variation of tissues or organs obtained from the necropsy. Therefore, compared with the parent virulent strain, PRV PRV-ZJ01 strain, PRV PRV-ZJ01-R strain displayed a significant reduction of pathogenicity, and was an artificially attenuated virus strain.

According to the immunogenicity assay, it revealed that the culture of the $110^{th}$ passage of PRV PRV-ZJ01-R strain can still maintain excellent immunogenicity. The piglets, on day 21 after inoculation, can be protected against the virulent strain, PRV PRV-ZJ01 strain. Meanwhile, the piglets, which were not inoculated with the culture of PRV-ZJ01-R strain, cannot resist the attack from PRV PRV-ZJ01 strain, and all displayed the disease.

It showed in the reversion of virulence assay that, after inoculation of the cultures of the $1^{st}$ to $110^{th}$ passages of virus in pig herd, no reversion of virulence of the virus was found during passage of the viruses through continuous contact of pigs. Therefore, the safety of the vaccines can be ensured since the virus, after being inoculated into pig herd, would not evolve into a virulent virus which is able to cause disease.

As a preferred embodiment of the present invention, the attenuated strain of PRV HeN1 strain was obtained through the method of attenuating the pseudorabies virus according to the invention, named PRV HeN1-R strain. Compared with PRV HeN1 strain, the genes of PRV HeN1-R strain have continuous deficiency of gI/gE/11K/28K genes (3455 bp in total), in which the site and size of deleted genes are totally the same as those of PRV HN1201-R strain.

The pathogenicity test indicated that the cultures of the $1^{st}$ passage to $110^{th}$ passage of PRV HeN1-R displayed a significant reduction of pathogenicity in pigs. During the observation of piglets for 28 days after inoculation, there were no clinical signs, or no changes in tissues or organs obtained from the necropsy. Therefore, compared with the parent virulent strain, PRV HeN1 strain, PRV HeN1-R strain displayed a significant reduction of pathogenicity, and was an artificially attenuated virus strain.

According to the immunogenicity assay, it revealed that the culture of the $110^{th}$ passage of PRV HeN1-R strain can still maintain excellent immunogenicity. The piglets, on day 21 after inoculation, can be protected against the virulent strain, PRV HeN1 strain. Meanwhile, the piglets, which were not inoculated with the culture of HeN1-R strain, cannot resist the attack from PRV HeN1 strain, and all displayed the disease.

It showed in the reversion of virulence assay that, after inoculation of the cultures of the $1^{st}$ to $110^{th}$ passages of virus in pig herd, no reversion of virulence of the virus was found during passage of the viruses through continuous contact of pigs. Therefore, the safety of the vaccines can be ensured since the virus, after being inoculated into pig herd, would not evolve into a virulent virus which is able to cause disease.

As a preferred embodiment of the present invention, the attenuated strain of PRV JS-2012 strain was obtained through the method of attenuating the pseudorabies virus according to the invention, named PRV JS-2012-R strain. Compared with PRV JS-2012 strain, the genes of PRV JS-2012-R strain have continuous deficiency of gI/gE/11K/28K genes (3455 bp in total), in which the site and size of deleted genes are totally the same as those of PRV JS-2012-R strain.

The pathogenicity test indicated that the cultures of the $1^{st}$ passage to $110^{th}$ passage of PRV JS-2012-R displayed a significant reduction of pathogenicity in pigs. During the observation of piglets for 28 days after inoculation, there were no clinical signs, or no changes in tissues or organs obtained from the necropsy. Therefore, compared with the parent virulent strain, i.e. PRV JS-2012 strain, PRV JS-2012-R strain displayed a significant reduction of pathogenicity, and was an artificially attenuated virus strain.

According to the immunogenicity assay, it revealed that the culture of the $110^{th}$ passage of PRV JS-2012-R strain can still maintain excellent immunogenicity. The piglets, on day 21 after inoculation, can be protected against the virulent strain, PRV JS-2012 strain. Meanwhile, the piglets which were not inoculated with the culture of JS-2012-R strain cannot resist the attack from PRV JS-2012 strain, and all displayed the disease.

It showed in the reversion of virulence assay that, after inoculation of the cultures of the $1^{st}$ to $110^{th}$ passages of virus in pig herd, no reversion of virulence of the virus was found during passages of the viruses through continuous contact of pigs. Therefore, the safety of the vaccines can be ensured since the virus, after being inoculated into pig herd, would not evolve into a virulent virus which is able to cause disease.

As used herein, the term "variant strain of pseudorabies virus", also called highly pathogenic PRV strain, refers to a strain able to cause significant manifestations including infection among swine at any ages, horizontal transmission among swine herds, short incubation period (1~2 days), a morbidity rates between 10%~100%, a mortality rate in pigs between 10%~100% (a mortality rate in piglets can reach up to 100%), high fever of pigs after being infected (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their forelimbs, and finally dying of exhaustion, and reproductive disorder symptoms caused by the infection such as declined semen quality of boar, as well as abortion of pregnant sow (the abortion rate can reach up to 35%), premature birth, stillbirth, weakened piglets (weakened piglets all die by 14 days of age), etc.

Preferably, said variant strain of pseudorabies virus is obtained through isolation, and when infection with said variant strain recurs in pigs previously immunized with attenuated gene-deleted strain of pseudorabies virus according to the prior art, the pigs still display clinical signs of infection with said variant strain, selected from high fever, depression and partial or complete loss of appetite.

Preferably, said variant strain of pseudorabies virus is a virus strain of which gE protein has the sequence of SEQ ID NO. 3 or shares at least 95% homology to the sequence of SEQ ID NO. 3.

Preferably, said variant strain of pseudorabies virus is such a variant strain of pseudorabies virus that when infection with said variant strain recurs in pigs previously immunized with attenuated strain of PRV with deficiency of one or more of gE, TK and gI genes, according to the prior art, the pigs are still infected with pseudorabies, which optionally causes clinical signs of infection, selected from depression and loss of appetite among piglets at the age of 9-10 days.

The term "homology" in the present invention refers to the level of similarity between two amino acid sequences or two nucleotide sequences. The homology between amino acid sequences or nucleotide sequences can be calculated by any appropriate methods well known in the art, for example, the target amino acid (or nucleotide) sequence and the reference amino acid (or nucleotide) sequence are aligned, and gaps can be induced if necessary, so as to optimize the number of the identical amino acids (or nucleotides) between two aligned sequences, and the percentage of the identical amino acids (or nucleotides) between two aligned sequences can be calculated accordingly. Alignment of amino acid (or nucleotide) sequences and calculation of homology can be achieved by software well known in the art. Examples of such software include, but are not limited to, BLAST (which can be accessed through the website of the National Center for Biotechnology Information, NCBI, or can be found in Altschul S. F. et al, J. Mol. Biol, 215:403-410 (1990); Stephen F. et al, Nucleic Acids Res., 25:3389-3402(1997)), ClustalW2 (which can be accessed through the website of the European Bioinformatics Institute, EBI, or can be found in Higgins D. G. et al, Methods in Enzymology, 266:383-402(1996); Larkin M. A. et al, Bioinformatics (Oxford, England), 23(21):2947-8(2007)), and TCoffee (which can be accessed through the website of the Swiss Institute of Bioinformatics, SIB, or can be found in, Poirot O. et al, Nucleic Acids Res., 31(13):3503-6(2003); Notredame C. et al, J. Mol. Boil, 302(1):205-17(2000)) etc. It is all within the knowledge scope of a person skilled in the art that when using the software to do sequence alignment, he can use the default parameters provided by the software or adjust the parameters provided by the software according to the actual condition. The above-mentioned content is apprehensible for the person skilled in the art.

The term "gI protein" is encoded by US7, which comprises 366 amino acids.

The term "gE protein" is encoded by US8, which comprises 579 amino acids.

The term "11K protein" is encoded by US9, which comprises 98 amino acids.

The term "28K protein" is encoded by US2, which comprises 256 amino acids.

The term "gI/gE/11K/28K" in the present invention refers to "gI, gE, 11K and 28K", wherein "/" in the present invention refers to "and", for example, "inactivation of gI/gE/11K/28K proteins" refers to all of gI, gE, 11K and 28K proteins.

Unless otherwise stated, the term "PRV-gI⁻/gE⁻/11K⁻/28K⁻" in the present invention refers to deficiency of gI, gE, 11K and 28K genes.

The continuous deficiency of gI/gE/11K/28K genes causes the inactivation of the corresponding function of gI/gE/11K/28K genes, which can also be achieved by using well known methods in the art, including deficiency of nucleotide sequence expressing the functional fragments of those above proteins from the gene, deletion of the whole ORF from the gene, or deletion or addition of one or more nucleotides whereby the gene cannot express functional proteins normally or the proteins expressed don't have their original function or have an extremely weak function.

Another aspect of the present invention relates to a method for preparing the vaccine composition, wherein said method comprises the steps: (1) said attenuated strain of porcine pseudorabies virus or the culture thereof is amplified and cultured to obtain the amplified attenuated strain of porcine pseudorabies virus; and (2) a carrier is added into said amplified attenuated strain of porcine pseudorabies virus.

As a preferred embodiment of the present invention, said culture of attenuated strain of porcine pseudorabies virus is a culture within $1^{st}$~$110^{th}$ passages.

As a preferred embodiment of the present invention, in said method for preparing said vaccine composition, said method comprises the steps: (1) said attenuated strain of porcine pseudorabies virus is cultured; and (2) a cryoprotectant is added into said attenuated strain of cultured porcine pseudorabies virus.

Another aspect of the present invention relates to a prepared vaccine composition, wherein the content of said attenuated strain of porcine pseudorabies virus is not less than $10^{6.0}$ $TCID_{50}$/piglet.

As a preferred embodiment of the present invention, in the vaccine composition prepared according to the invention, the content of said attenuated strain of porcine pseudorabies virus is in the range of $10^{6.0}$ $TCID_{50}$/piglet~$10^{7.0}$ $TCID_{50}$/piglet.

As a preferred embodiment of the present invention, the antigen of said attenuated strain of porcine pseudorabies virus is PRV HN1201-R strain.

As a preferred embodiment of the present invention, the antigen of said attenuated strain of porcine pseudorabies virus is PRV HN1202-R strain.

As a preferred embodiment of the present invention, the antigen of said attenuated strain of porcine pseudorabies virus is PRV Fa-R strain.

As a preferred embodiment of the present invention, the antigen of said attenuated strain of porcine pseudorabies virus is PRV PRV-ZJ01-R strain.

As a preferred embodiment of the present invention, the antigen of said attenuated strain of porcine pseudorabies virus is PRV HeN1-R strain.

As a preferred embodiment of the present invention, the antigen of said attenuated strain of porcine pseudorabies virus is PRV JS-2012-R strain.

Preferably, said vaccine composition further comprises a cryoprotectant.

Optionally, one or more compounds with adjuvant activity may be added to vaccines. It does not necessarily require such an adjuvant to achieve the efficacy of the live attenuated pseudorabies virus according to the present invention, but especially for a combination vaccine comprising the live attenuated pseudorabies virus according to the present invention and antigenic materials from another pathogenic virus or microorganism (see below), it will be worth adding an adjuvant. Adjuvants are non-specific stimulators of the immune system. They improve immune response of the host responding to a vaccine. Examples of adjuvants known in the art include complete/incomplete Freund's adjuvant, vitamin E, non-ionic blocking copolymers, muramyl dipeptide, ISCOMs (immune stimulating complexes, refer to, for example the European patent EP 1099 42), saponins, mineral oil, vegetable oil, and Carbopol.

Therefore, in a preferred form of said embodiment, the live attenuated vaccine according to the present invention further comprises an adjuvant.

Other examples of pharmaceutically acceptable carriers or diluents, which can be used in the present invention include stabilizers such as SPGA, carbohydrates (e.g., sorbitol, mannitol, starch, sucrose, glucose, dextran), proteins such as albumin or casein, protein-containing agents such as bovine serum or skimmed milk and buffers (e.g. phosphate buffer).

Especially when such stabilizers are added to the vaccine, the vaccine is very suitable for freeze-drying. Therefore, in a more preferred form of said embodiment, the live attenuated vaccine is in a freeze-dried form.

As a preferred embodiment of the present invention, said vaccine composition further comprises antigen of classical swine fever virus, antigen of porcine reproductive and respiratory syndrome virus, antigen of porcine circovirus, antigen of *haemophilus parasuis*, antigen of *mycoplasma hyopneumoniae*, antigen of porcine parvovirus and antigen of porcine encephalitis virus. In addition, said pseudorabies vaccine in the present invention can be used conjunctly with other inactivated pathogens or antigen to prepare combined vaccines or complex vacancies against various diseases including pseudorabies.

As used herein, the term "combined vaccine" refers to a vaccine prepared with the virus mixture by mixing the pseudorabies virus in the present invention with at least one different virus.

The term "complex vaccine" refers to a vaccine prepared from viruses and bacterium. For example, the pseudorabies virus in the present invention can be mixed or combined with classical swine fever virus, porcine reproductive and respiratory syndrome virus, porcine circovirus and/or *haemophilus parasuis* and *mycoplasma.*

As an embodiment of the present invention, said vaccine further comprises inactivated pathogens or antigen.

Preferably, said antigen comprises antigen of classical swine fever virus, antigen of porcine reproductive and respiratory syndrome virus, antigen of porcine circovirus and/or *haemophilus parasuis* or antigen of *mycoplasma hyopneumoniae.*

As an embodiment of the present invention, the attenuated virus strain in the present invention can be inserted by exogenous genes, said exogenous genes encode one or more antigens selected from a plurality of pathogens infecting pigs, said pathogens consist of porcine reproductive respiratory syndrome (PRRS) virus, porcine Influenza virus, porcine parvovirus, transmissible gastroenteritis virus, rotavirus, type 1 or type 2 porcine circovirus virus, *Escherichia coli, Erysipelothrix rhusi opathiae, Bordetella bronchiseptica, Haemophilus parasuis, Mycoplasma hyopneumoniae* and *Streptococcus suis.*

As an embodiment of the present invention, genes encoding the above-mentioned antigens are inserted in the deficiency region of gI/gE/11K/28K of the attenuated virus strain according to the present invention as exogenous genes.

Preferably, said vaccine composition may further comprise medium, adjuvants and excipients.

The vaccine composition according to the present invention may also comprise medium, adjuvants and/or excipients. Physiological saline or distilled water can be used as medium.

The amount of the ingredients or components of the composition in the present invention is preferably a therapeutically effective amount. The therapeutically effective amount refers to the required amount for exerting their immunological effects in a host where the composition is administered, without causing the side effects due to an excessive amount. The ingredients to be used and the accurate amount of composition to be administered may vary depending on factors such as the type of diseases to be treated, the type of animals to be treated and their age and way of administration, and other ingredients in the composition.

Another aspect of the present invention relates to a use of said vaccine composition for preparing medicine for treatment and prevention of diseases related to the pseudorabies virus.

As an embodiment of the present invention, said pseudorabies is pseudorabies caused by the variant strain of pseudorabies virus.

As used herein, the term "diseases related to the pseudorabies virus" can further refer to diseases with significant manifestations including but not limited to infection among swine at any ages, horizontal transmission among swine herds, short incubation period (1-2 days), morbidity rates between 10%~100%, mortality rate in pigs between 10%~100% (mortality rate in piglets can reach up to 100%), high fever of pigs after being infected (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their forelimbs, and finally dying of exhaustion, and reproductive disorder symptoms caused by infection such as declined semen quality of boar, as well as abortion of pregnant sow (the abortion rate can reach up to 35%), premature birth, stillbirth, weakened piglets (weakened piglets die by 14 days of age), etc. The differences between above described symptoms and symptoms caused by infection of regular pseudorabies virus in the prior art are: in adult pigs (whose weight is above 50 kg), high fever of infected pigs (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their forelimbs, and finally dying of exhaustion; sudden incidence of pseudorabies in newborn piglets and piglets below the age of 4 weeks, further resulting in massive death with a mortality rate of more than 90%; main manifestations in infected piglets including increased body temperature over 41° C., complete loss of appetite, obvious neurological signs and diarrhea; and in piglets just before or after being weaned, mainly respiratory symptoms, such as dyspnea, coughing and runny noses, etc.

As used herein, the term "prevention" refers to all behaviors to inhibit the infection of pseudorabies virus or delay the onset of the disease via administration of the vaccine composition according to the present invention. The term "treatment" refers to all behaviors to relieve or cure the symptoms caused by infection of PRV via administration of the vaccine composition according to the present invention.

Prominent advantages of the present invention (1) The virulent genes were naturally deleted from the strain in the present invention via a way of natural passage, so that the gene-deleted strain can be better compatible with the nature, without any risk of reversion of virulence, leading to a good biosafety.

(2) As shown in the results, the method for attenuating the wild virus according to the present invention is rather stable, operable and repeatable, which provides a different way to attenuating virulent virus strain.

(3) The strain in the present invention with less virulence can provide better immune protection, and induce an earlier production of antibodies.

(4) The gI/gE/11K/28K gene deficiency region of the strain in the present invention, could be inserted by different exogenous genes according to conventional biology technology to constitute corresponding recombinant viruses, resulting in a beneficial prospect of application.

SEQUENCE LISTING

SEQ ID NO. 1 is the nucleotide sequence of the fragment deleted during the process of attenuating PRV HN1201-R strain.

SEQ ID NO. 2 is the amino acid sequence of gI protein in the fragment deleted from PRV HN1201-R strain.

SEQ ID NO. 3 is the amino acid sequence of gE protein in the fragment deleted from PRV HN1201-R strain.

SEQ ID NO. 4 is the amino acid sequence of 11K protein in the fragment deleted from PRV HN1201-R strain.

SEQ ID NO. 5 is the amino acid sequence of 28K protein in the fragment deleted from PRV HN1201-R strain.

DETAILED DESCRIPTION

The description of the present invention is further provided as follows with reference to the specific embodiments, and features and advantages of the present invention will become more apparent from the following description. However, these embodiments are only exemplary, but not forming any limitation to the scope of the present invention. It should be understood by a person skilled in the art that modifications or alternatives to details and forms of the technical solution of the present invention without deviation from the spirit and scope of the present invention will be allowed, while those modification and alternatives should all fall within the scope of protection of the present invention.

In the embodiments of the present invention, PRV HN1201 strain, HN1202 strain, Fa strain, PRV-ZJ01 strain, HeN1 strain and JS-2012 strain are used as examples to illustrate the present invention.

In the invention, the term "per pig" refers to the amount of vaccine each pig is injected.

In the invention, the term "$TCID_{50}$" refers to 50% tissue culture infective dose, a way to represent viral infectivity.

Dulbecco's Modified Eagle's Medium (DMEM) in the present invention is prepared with DMEM dry powdered medium (Gibco) according to the instruction.

In the present invention, the term "PBS" is the abbreviation for Phosphate Buffer Saline, and 0.01 mM pH 7.4 PBS as used in the present invention was prepared as described in *Molecular cloning: Laboratory manuals, 3rd edition.*

Fetal bovine serum was purchased from PAA.

The PRV HN1201 strain (Pseudorabies virus, strain HN1201) used in the present embodiments was deposited in the China Type Culture Collection Center on May 20, 2013, of which the accession number is CCTCC NO. V 201311 and the address of depositary is Wuhan University, Wuhan City, Hubei Province.

The PRV HN1202 strain (Pseudorabies virus, strain HN1202) used in the present embodiments was deposited in the China Type Culture Collection Center on Aug. 26, 2013 of which the accession number is CCTCC NO. V 201335 and the address of depositary is Wuhan University, Wuhan City, Hubei Province.

The PRV HN1201-R strain (Pseudorabies virus, strain HN1201-R) used in the present embodiments was deposited in the China Type Culture Collection Center on Mar. 17, 2015 of which the accession number is CCTCC NO. V 201516 and the address of depositary is Wuhan University, Wuhan City, Hubei Province.

"PRV" is the abbreviation for the term "pseudorabies virus".

Marc-145 cells were purchased from ATCC.

DF-1 cells were purchased from ATCC.

Example 1: Acquisition of PRV HN1201-R Strain

1. The well-grown Marc-145 cells digested with trypsin, were inoculated in cell culture flasks and then cultured at 36° C.~38° C. with cell growth medium (pH was adjusted to 7.0~8.0) containing 90%~97% (V/V) DMEM culture medium and 3%~10% (V/V) fetal bovine serum, to form a proper monolayer for inoculation with virus.
2. The PRV HN1201 strain was inoculated into the above well-grown monolayer of subcultured cells, and the cells continued to be cultured at 36° C.~38° C. with cell maintenance medium (pH was adjusted to 7.1~7.5) containing 95%~99% (V/V) DMEM and 1%~5% (V/V) fetal bovine serum. After 40 h~48 h, the cell medium containing viruses, i.e. the pseudorabies virus strain adapted to mammalian cells, was harvested when the cytopathic effect of cells reached 80%, as the virus seed for continued passage. Different passages of virus harvested, P1, P2, P3, P4, P5, P6, P7, P8, P9, P10, P15, P20, P30, P50, P70, P90, P110, P130, P150 and P200, was sequenced respectively, with the results indicating no deficiency of genes for each passage.
3. The well-grown DF-1 cells digested with trypsin, were inoculated in cell culture flasks and then cultured at 36° C.~38° C. with cell growth medium (pH was adjusted to 7.0~8.0) containing 90%~97% (V/V) DMEM and 3%~10% (V/V) fetal bovine serum, to form a proper monolayer for inoculation with virus.
4. Different passages of the pseudorabies virus strain adapted to mammalian cells harvested in the step 2, was inoculated into the above well-grown monolayer of subcultured DF-1 cells obtained from the step 3, and continued to be cultured at 36° C.~38° C. with cell maintenance medium (pH was adjusted to 7.1~7.5) containing 95%~99% (V/V) DMEM and 1%~5% (V/V) fetal bovine serum. After 40 h~48 h, the cell medium containing viruses was harvested respectively when the cytopathic effect of cells reached 80%, i.e. P1-1, P2-1, P3-1, P4-1, P5-1, P6-1, P7-1, P8-1, P9-1, P10-1, P15-1, P20-1, P30-1, P50-1, P70-1, P90-1, P110-1, P130-1, P150-1, P200-1. Each passage of viruses harvested was sequenced respectively, with the results indicating that there was no deficiency of genes for P1-1, P2-1, P3-1, P4-1, while P5-1, P6-1, P7-1, P8-1, P9-1, P10-1, P15-1, P20-1, P30-1, P50-1, P70-1, P90-1, P110-1, P130-1, P150-1 and P200-1 all has the deficiency of genes, in which each has continuous deficiency of 3455 bp started from the site of the $890^{th}$ nucleotide of gI gene.

In order to verify if it is related to passage times in DF-1 that there was no deficiency of genes for P1-1, P2-1, P3-1 and P4-1, such serial passage continued and P1-2, P1-3, P1-4, P1-5, P1-6, P1-7, P1-8, P1-9, P1-10, P2-2, P2-3, P2-4, P2-5, P2-6, P2-7, P2-8, P2-9, P2-10, P3-2, P3-3, P3-4, P3-5, P3-6, P3-7, P3-8, P3-9, P3-10, P4-2, P4-3, P4-4, P4-5, P4-6, P4-7, P4-8, P4-9 and P4-10 was harvested respectively. Each harvested virus was sequenced respectively, with the results indicating no deficiency of genes for each passage. It showed that in the case where PRV was passaged four times or less in Marc-145 cells, the occurrence of deficiency of genes was not related to passage times in DF-1, but to passage times of adaption in Marc-145 cells.

In order to verify the stability of continued passage in Df-1 for the viruses with deficiency of genes, P5-1, P6-1, P7-1, P8-1, P9-1, P10-1, P15-1, P20-1, P30-1, P50-1, P70-1, P90-1, P110-1, P130-1, P150-1, P200-1 was continued to be passaged, resulted to the harvest of P5-2, P5-3, P5-4, P5-5, P5-6, P5-7, P5-8, P5-9, P5-10, P6-2, P6-3, P6-4, P6-5, P6-6, P6-7, P6-8, P6-9, P6-10, P7-2, P7-3, P7-4, P7-5, P7-6, P7-7, P7-8, P7-9, P7-10, P8-2, P8-3, P8-4, P8-5, P8-6, P8-7, P8-8, P8-9, P8-10, P9-2, P9-3, P9-4, P9-5, P9-6, P9-7, P9-8, P9-9, P9-10, P10-2, P10-3, P10-4, P10-5, P10-6, P10-7, P10-8, P10-9, P10-10, P15-2, P15-3, P15-4, P15-5, P15-6, P15-7, P15-8, P15- 9, P15-10, P20-2, P20-3, P20-4, P20-5, P20-6, P20-7, P20-8, P20-9, P20-10, P30-2, P30-3, P30- 4, P30-5, P30-6, P30-7, P30-8, P30-9, P30-10, P50-2, P50-3, P50-4, P50-5, P50-6, P50-7, P50- 8, P50-9, P50-10, P70-2, P70-3, P70-4, P70-5, P70-6, P70-7, P70-8, P70-9, P70-10, P90-2, P90- 3, P90-4, P90-5, P90-6, P90-7, P90-8, P90-9, P90-10, P110-2, P110-3, P110-4, P110-5, P110-6, P110-7, P110-8, P110-9, P110-10, P130-2, P130-3, P130-4, P130-5, P130-6, P130-7, P130-8, P130-9, P130-10, P150-2, P150-3, P150-4, P150-5, P150-6, P150-7, P150-8, P150-9, P150-10, P200-2, P200-3, P200-4, P200-5, P200-6, P200-7, P200-8, P200-9 and P200-10. Each passage of harvested viruses was sequenced respectively, with the results indicating that there was no change for the occurrence of deficiency of genes for each passage, in which each always has continuous deficiency of 3455 bp started from the site of the $890^{th}$ nucleotide of gI gene, indicating a stable passage in DF-1 for the PRV gene-deleted strain.

The attenuated strain of PRV, P30-10 was named PRV HN1201-R strain.

Example 2: Study of Biological Characteristic of PRV HN1201-R Strain

1. Pathogenicity Test of the Virus 15 piglets at 7 days of age which were negative for pseudorabies antigens and antibodies were randomly divided into 3 groups (A, B and blank control groups), each with 5 piglets. The grouping and challenging conditions are shown in Table 1.

TABLE 1

Grouping of animals in the pathogenicity test

| Group | Strains used for inoculation | Dose of inoculation |
|---|---|---|
| A | HN1201-R strain | inoculated with 1 ml ($10^{7.0}TCID_{50}$/ml)/piglet by intranasal instillation |

TABLE 1-continued

| Grouping of animals in the pathogenicity test | | |
|---|---|---|
| Group | Strains used for inoculation | Dose of inoculation |
| B | HN1201 strain | inoculated with 1 ml ($10^{7.0}$TCID$_{50}$/ml)/piglet by intranasal instillation |
| Blank control | DMEM medium | inoculated with 1 ml/piglet by intranasal instillation |

Piglets were observed for 28 days after inoculation of virus, while the temperature of piglets was determined daily, and clinical signs and death status were observed. The specific results are shown in Table 2.

TABLE 2

| Pathogenicity of HN1201-R strains in 7-day-old piglets | | | |
|---|---|---|---|
| Group | Number | Clinical signs | Death status |
| A | A1 | Normal body temperature, no clinical signs | Survived |
| | A2 | Normal body temperature, no clinical signs | Survived |
| | A3 | Body temperature increased for 1 day, no other clinical signs | Survived |
| | A4 | Body temperature increased for 1 day, no other clinical signs | Survived |
| | A5 | Normal body temperature, no clinical signs | Survived |
| B | B1 | Body temperature increased for 4 days, depression, complete loss of appetite, remaining recumbent, dyspnea, trembling, convulsions; neurological signs such as turning around, and making strokes with their forelimbs, etc. | Died on day 4 after challenge |
| | B2 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | B3 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | B4 | Body temperature increased for 3 days, depression, complete loss of appetite, remaining recumbent, dyspnea, trembling; neurological signs such as convulsions, turning around, and making strokes with their forelimbs, etc. | Died on day 3 after challenge |
| | B5 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| Blank control | K1 | No abnormal clinical signs | Survived |
| | K2 | No abnormal clinical signs | Survived |
| | K3 | No abnormal clinical signs | Survived |
| | K4 | No abnormal clinical signs | Survived |
| | K5 | No abnormal clinical signs | Survived |

It showed in the results that inoculation with PRV HN1201 strain in 7-day-old piglets could lead to death with a morality rate of 100% (5/5) of inoculated piglets, while PRV HN1201-R strain displayed a significant reduction of virulence, only causing increased body temperature of two pigs, without any other clinical signs, or any change of tissues or organs obtained from the necropsy.

Through the pathogenicity test it indicated that compared with the parent virulent strain, i.e. PRV HN1201 strain, PRV HN1201-R strain displayed a significant reduction of pathogenicity, and was an attenuated virus strain.

Meanwhile, in order to verify the stability of pathogenicity of different passages of PRV HN1201-R strain, a group of piglets (5 piglets) at 7 days of age which were negative for pseudorabies antigens and antibodies were inoculated with the cultures of the $1^{st}$, $30^{th}$, $60^{th}$, $85^{th}$ and $110^{th}$ passages of PRV HN1201-R strain, respectively, and each was inoculated with 1 ml ($10^{7.0}$ TCID$_{50}$/ml) by intranasal instillation. Another five piglets were used as the control group. The clinical manifestations of piglets were observed and recorded daily until 28 days after inoculation of virus.

It showed in the results that, from the observation of piglets for 28 days after inoculation with the cultures of the $1^{st}$, $30^{th}$, $60^{th}$, $85^{th}$ and $110^{th}$ passages of PRV HN1201-R strain, PRV HN1201-R strain displayed a significant reduction of virulence, only causing increased body temperature of 1~2 pigs/group, without any other clinical signs, or any change of tissues or organs obtained from the necropsy.

Through the pathogenicity test of different passages, it indicated that different passages of PRV HN1201-R strain all displayed lower virulence.

2. Immunogenicity Assay

On the $21^{st}$ day after immunization, all of the five piglets inoculated with PRV 1201-R strain and five piglets in the control group were challenged with $1\times10^{7.0}$ TCID$_{50}$/piglet of PRV HN1201. After challenge, the body temperature of piglets was measured daily, and in the meanwhile clinical signs and death status were observed. The results are shown in Table 3.

TABLE 3

| Pathogenicity of HN1201-R strains in 7-day-old piglets | | | |
|---|---|---|---|
| Group | Number | Clinical signs | Rate of protection |
| A | A1 | Normal body temperature, normal appetite, no abnormal clinical signs, survived | 100% (5/5) |
| | A2 | Normal body temperature, normal appetite, no abnormal clinical signs, survived | |
| | A3 | Normal body temperature, normal appetite, no abnormal clinical signs, survived | |
| | A4 | Normal body temperature, normal appetite, no abnormal clinical signs, survived | |
| | A5 | Normal body temperature, normal appetite, no abnormal clinical signs, survived | |
| Blank control | K1 | Body temperature increased, depression, loss of appetite, significant clinical signs, died on day 4 after challenge | 0% (0/5) |
| | K2 | Body temperature increased, depression, complete loss of appetite, significant clinical signs, died on day 4 after challenge | |
| | K3 | Body temperature increased, depression, complete loss of appetite, significant clinical signs, died on day 3 after challenge | |

TABLE 3-continued

| Pathogenicity of HN1201-R strains in 7-day-old piglets | | | |
|---|---|---|---|
| Group | Number | Clinical signs | Rate of protection |
| | K4 | Body temperature increased, depression, loss of appetite, significant clinical signs, died on day 4 after challenge | |
| | K5 | Body temperature increased, depression, loss of appetite, significant clinical signs, died on day 4 after challenge | |

The result indicated that all the piglets inoculated with PRV HN1201-R strain were healthy and alive, while all from the control group died.

According to the immunogenicity assay, the PRV HN1201-R strain can provide excellent protection against PRV HN1201 strain, showing excellent immunogenicity.

Meanwhile, in order to verify the stability of immunogenicity of different passages of PRV HN1201-R strain, on the $21^{st}$ day after immunization, all the immune groups inoculated with the cultures of the $1^{st}$, $30^{th}$, $60^{th}$, $85^{th}$ and $110^{th}$ passages of PRV HN1201-R strain as well as the control group were challenged with $1\times10^{7.0}$ $TCID_{50}$/piglet of PRV HN1201. After challenge, the body temperature of piglets was determined daily, and in the meanwhile clinical signs and death status were observed.

The result indicated that all the piglets inoculated with the cultures of the $1^{st}$, $30^{th}$, $60^{th}$, $85^{th}$ and $110^{th}$ passages of PRV HN1201-R strain were alive, while all from the control group died.

According to the immunogenicity assay of different passages, different passages of PRV HN1201-R strain all can provide excellent protection against PRV HN1201 strain, showing excellent immunogenicity.

3. Reversion of Virulence Test of the Virus 30 piglets at 7 days of age which were negative for pseudorabies antigens and antibodies were randomly divided into 5 groups, each with 6 piglets. 6 piglets of Group 1 which were negative for pseudorabies antigens and antibodies were inoculated with $10^{7.0}$ $TCID_{50}$/piglet of the cultures of PRV HN1201-R strain (the $1^{st}$, $30^{th}$, $60^{th}$, $85^{th}$, $110^{th}$ passages and the $1^{st}$+$30^{th}$+$60^{th}$+$85^{th}$+$110^{th}$ passages) respectively by intranasal instillation. On day 14, they were raised together with the 6 piglets of Group 2 which were negative for pseudorabies antigens and antibodies. 14 days later, the 6 piglets of Group 1 were drawn back, and again, the 6 piglets of Group 3, which were negative for pseudorabies antigens and antibodies, were raised together with the 6 piglets of Group 2 and so on. After 4 serial passages, all the drawn piglets were killed in order to observe if there were any pathological changes.

It showed in the result that no abnormal changes were found during the clinical observation and gross anatomy of 30 experimental piglets by the 4th serial passage of the co-habitation infection experiment, indicating that there was no reversion of virulence of this attenuated strain. Therefore, the safety of the vaccines can be ensured since the virus, after being inoculated into piglets, would not evolve into a virulent virus which is able to cause disease.

4. Genes Sequences Analysis

The genome amplification of the cultures of the $1^{st}$ passage to $110^{th}$ passage of PRV HN1201-R strain was accomplished by means of RT-PCR (The genomic DNA of culture of different passages was amplified respectively). The product acquired from amplification was recovered, purified, and linked to the plasmid vector for sequencing, so that the nucleotide sequence of the viral gene was determined and transformed through computer software into the amino acid sequence of the virus. The obtained amino acid sequence was compared with the amino acid sequence of the parent virulent strain, HN1201 strain via sequence analysis software, and the amino acids sequence of the virus was characterized.

It showed in the results that for the cultures of the $1^{st}$ passage to $110^{th}$ passage of PRV HN1201-R strain, each amino acid sequences encoded by the viral genes commonly has continuous deficiency of gI/gE/11K/28K genes (3455 bp in total), i.e. continuous deficiency of 3455 bp started from the site of the $890^{th}$ nucleotide of gI gene. The deleted sequence is as shown in SEQ No. 1.

It indicated that a common characteristic change of the amino acids sequences encoded by the viral genes of the culture of different passages of PRV HN1201-R strain might be the reason for the reduction of virulence of the parent virulent strain.

Example 3: Preparation of the Attenuated Live Vaccine of PRV HN1201-R Strain

1. Proliferation of Virus

The virus seed of PRV HN1201-R strain prepared in Example 1 was diluted at $5\times10^4$ fold, and then inoculated into a monolayer of ST cell. After 1 h adhesion, 1000 ml of DMEM medium containing 2% fetal calf serum was added into ST cell, which was then placed at 37° C. in a roller bottle with a rotation speed of 6 rph. The cell medium containing viruses was harvested when the cytopathic effect of cells reached 80%; the viruses were harvested after 2 times of freezing-thawing the medium, and the virus titer was assessed. The virus solution was preserved at low temperature.

2. Preparation of a Protective Agent 40 g of sucrose and 8 g of gelatin was added into every 100 ml of deionized water, and the solution was autoclaved (under 121° C. for 30 min) after being fully melted.

3. Preparation of Vaccine

The virus solution prepared and preserved from above procedure was mixed with the protective agent prepared and preserved from above procedure at a volume ratio of 1:1 and the mixed virus solution was freeze-dried. The specific ratio of content of the vaccine is shown in Table 4.

TABLE 4

| ratio of content of the attenuated live vaccine of PRV HN1201-R strain | | |
|---|---|---|
| | Group | |
| | Vaccine 1 ($TCID_{50}$) | Vaccine 2 ($TCID_{50}$) |
| Antigen of HN1201-R strain | $10^{6.0}$ | $10^{7.0}$ |
| protective agent (V/V) | 50% | 50% |

Example 4: Immunogenicity Assay of the Attenuated Live Vaccine of HN1201-R Strain 15 9-day-old piglets which were negative for PRV antibodies and PRV antigens were randomly divided into 3 groups, each with 5 piglets, and the piglets were injected with the attenuated live PRV HN1201-R strain prepared in Example 3. The first group was inoculated with Vaccine 1, and the second group was inoculated with Vaccine 2, and the third group was the control group. The piglets were challenged with $1\times10^{7.0}$ $TCID_{50}$/piglet of PRV HN1201 strain on day 21 after immunization. After challenge, the body temperature of piglets was measured daily, and in the meanwhile clinical signs and death status were observed. The results are shown in Table 5.

TABLE 5

Results of Immunogenicity assay of the attenuated live vaccine of HN1201-R strain

| Group | Number of piglets | Dose of Challenge | Clinical signs and death status | Rate of protection |
|---|---|---|---|---|
| Vaccine 1 | 5 | $10^{7.0}TCID_{50}$/piglet of HN1201 strain | Normal body temperature, normal appetite, no abnormal clinical signs, survived | 100% (5/5) |
| Vaccine 2 | 5 | $10^{7.0}TCID_{50}$/piglet of HN1201 strain | Normal body temperature, normal appetite, no abnormal clinical signs, survived | 100% (5/5) |
| Control group | 5 | $10^{7.0}TCID_{50}$/piglet of HN1201 strain | All the pigs displayed symptoms like increased body temperature, depression, partial or complete loss of appetite, and significant clinical signs; two died on day 3 after challenge, and all died within 4 days after challenge. | 0% (0/5) |

The result indicated that immunizing piglets with the attenuated live vaccine of PRV HN1201-R strain prepared in example 3 can block virus infection (i.e. prevent occurrence of clinic signs), and provide 100% (5/5) protection rate for piglets, while all the piglets in the blank control group died by day 4 after challenge.

It has proven that the attenuated live vaccine of PRV HN1201-R strain in two experimental groups can provide excellent protection, showing excellent immune protection and safety; in the meanwhile it indicated that PRV strain which has a continuous deficiency of gI/gE/11K/28K genes (3455 bp in total) would still maintain excellent immunogenicity.

Example 5: Immunogenicity Comparison Assay of the Attenuated Live Vaccine of HN1201-R Strain 15 9-day-old piglets which were negative for PRV antibodies and PRV antigens were randomly divided into 3 groups, each with 5 piglets. The first group was inoculated with Vaccine 1, the attenuated live vaccine of HN1201-R strain prepared in Example 3; the second group was immunized with the live PRV vaccine, Bartha K-61 strain purchased from HIPRA, Spain, with Batch No. 42RH; and the third group is the blank control group. The piglets were challenged with $1\times10^{7.0}$ $TCID_{50}$/piglet of PRV HN1201 strain on day 28 after immunization. After challenge, the body temperature of piglets was determined daily, and clinical signs and death status were observed as well. The detailed results are shown in Table 6.

TABLE 6

Results of Immunogenicity comparison assay of the attenuated live vaccine of HN1201-R strain

| Group | Number of piglets | Dose of challenge | Clinical signs and death status | Rate of protection |
|---|---|---|---|---|
| Vaccine 1 | 5 | $10^{7.0}TCID_{50}$/piglet of HN1201 strain | Normal body temperature, normal appetite, no abnormal clinical signs, survived | 100% (5/5) |
| Control vaccine | 5 | $10^{7.0}TCID_{50}$/piglet of HN1201 strain | Three pigs displayed symptoms like increased body temperature for 7-10 days, depression, and loss of appetite; one died. | 80% (4/5) |
| Blank control group | 5 | $10^{7.0}TCID_{50}$/piglet of HN1201 strain | All the pigs displayed symptoms like increased body temperature, depression, complete or partial loss of appetite, and significant clinical signs; two died on day 3 after challenge, and all died within 4 days after challenge. | 0% (0/5) |

The result indicated that immunizing piglets with the attenuated live vaccine of PRV HN1201-R strain prepared in Example 3 can block virus infection (i.e. prevent occurrence of clinic signs), and provide 100% (5/5) protection rate for piglets; all the piglets in the control group died by day 4 after challenge; whereas the commercial vaccines in the prior art cannot provide full protection for pigs.

It has proven that the attenuated live vaccine of PRV HN1201-R strain can provide excellent protection, showing better immune protection and safety than the commercial vaccines in the prior art.

Example 6: Acquisition of PRV HN1202-R Strain and Fa-R Strain

PRV HN1202 strain and Fa strain were subcultured respectively according to the procedures in Example 1, so as to obtain their attenuated PRV strains, named PRV HN1202-R strain and Fa-R strain.

Example 7: Study of Biological Characteristic of PRV HN1202-R Strain and Fa-R Strain 1. Pathogenicity Test of the Virus 20 piglets at 7 days of age which were negative for pseudorabies antigens and antibodies were randomly divided into 4 groups (C, D, E and F), each with 5 piglets; another 10 piglets were used as the blank control group. The grouping and challenging conditions are shown in Table 7.

TABLE 7

Grouping of the animals in the pathogenicity test for HN1202-R strain and Fa-R strain

| Group | Strain used for inoculation | Dose of inoculation |
|---|---|---|
| C | HN1202-R strain | inoculated with 1 ml ($10^{7.0}TCID_{50}$/ml)/piglet by intranasal instillation |

TABLE 7-continued

Grouping of the animals in the pathogenicity test for HN1202-R strain and Fa-R strain

| Group | Strain used for inoculation | Dose of inoculation |
|---|---|---|
| D | HN1202 strain | inoculated with 1 ml ($10^{7.0}TCID_{50}$/ml)/piglet by intranasal instillation |
| E | Fa-R strain | inoculated with 1 ml ($10^{7.0}TCID_{50}$/ml)/piglet by intranasal instillation |
| F | Fa strain | inoculated with 1 ml ($10^{7.0}TCID_{50}$/ml)/piglet by intranasal instillation |
| Blank control | DMEM medium | inoculated with 1 ml/piglet by intranasal instillation |

Piglets were observed for 28 days after inoculation of virus, while the temperature of piglets was measured daily, and clinical signs and death status were observed. The results are shown in Table 8.

TABLE 8

Pathogenicity of HN1202-R strains and Fa-R strain to 7-day-old piglets

| Group | Number | Clinical signs | Death status |
|---|---|---|---|
| C | C1 | Body temperature increased for 1 day, no clinical signs | Survived |
| | C2 | Normal body temperature,, no clinical signs | Survived |
| | C3 | Body temperature increased for 1 day, no other clinical signs | Survived |
| | C4 | Normal body temperature,, no clinical signs | Survived |
| | C5 | Body temperature increased for 1 day, no other clinical signs | Survived |
| D | D1 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | D2 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | D3 | Body temperature increased for 5 days, depression, complete loss of appetite, remaining recumbent, dyspnea, trembling; neurological signs such as convulsions, turning around, and making strokes with their forelimbs, etc. | Died on day 5 after challenge |
| | D4 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | D5 | Body temperature increased for 3 days, depression, complete loss of appetite, remaining recumbent, dyspnea, trembling; neurological signs such as convulsions, turning around, and making strokes with their forelimbs, etc. | Died on day 3 after challenge |

TABLE 8-continued

Pathogenicity of HN1202-R strains and Fa-R strain to 7-day-old piglets

| Group | Number | Clinical signs | Death status |
|---|---|---|---|
| E | E1 | Body temperature increased for 1 day, no clinical signs | Survived |
| | E2 | Body temperature increased for 1 day, no other clinical signs | Survived |
| | E3 | Body temperature increased for 1 day, no other clinical signs | Survived |
| | E4 | Normal body temperature,, no clinical signs | Survived |
| | E5 | Body temperature increased for 1 day, no other clinical signs | Survived |
| F | F1 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | F2 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | F3 | Body temperature increased for 5 days, depression, complete loss of appetite, remaining recumbent, dyspnea, trembling; neurological signs such as convulsions, turning around, and making strokes with their forelimbs, etc. | Died on day 5 after challenge |
| | F4 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | F5 | Body temperature increased for 5 days, depression, complete loss of appetite, remaining recumbent, dyspnea, trembling; neurological signs such as convulsions, turning around, and making strokes with their forelimbs, etc. | Died on day 5 after challenge |
| Blank control | K6 | no abnormal clinical signs | Survived |
| | K7 | no abnormal clinical signs | Survived |
| | K8 | no abnormal clinical signs | Survived |
| | K9 | no abnormal clinical signs | Survived |
| | K10 | no abnormal clinical signs | Survived |
| | K11 | no abnormal clinical signs | Survived |
| | K12 | no abnormal clinical signs | Survived |
| | K13 | no abnormal clinical signs | Survived |
| | K14 | no abnormal clinical signs | Survived |
| | K15 | no abnormal clinical signs | Survived |

It showed in the results that inoculation with PRV HN1202 strain in 7-day-old piglets could lead to death of 100% (5/5) of inoculated piglets, while PRV HN1202-R strain displayed a significant reduction of virulence, only causing increased body temperature of three pigs, without any other clinical signs, or any changes of tissues or organs obtained from the necropsy; inoculation with PRV Fa strain in 7-day-old piglets could lead to death of 100% (5/5) of inoculated piglets, while PRV Fa-R strain displayed a significant reduction of virulence, only causing increased body temperature of four pigs, without any other clinical signs, or any changes of tissues or organs obtained from the necropsy.

Through the pathogenicity test it indicated that compared with the parent virulent strain, i.e. PRV HN1202 strain, PRV HN1202-R strain displayed a significant reduction of pathogenicity; and was an attenuated virus strain; compared with the parent virulent strain, i.e. PRV Fa strain, PRV Fa-R strain displayed a significant reduction of pathogenicity, and was an attenuated virus strain.

Meanwhile, in order to verify the stability of pathogenicity of different passages of PRV HN1202-R strain and Fa-R strain, a group (5) of piglets at 7 days of age which were negative for pseudorabies antigens and antibodies were inoculated with 1 ml ($10^{7.0}$ $TCID_{50}$/ml) of the cultures of $1^{st}$, $30^{th}$, $60^{th}$, $85^{th}$ and $110^{th}$ passages of PRV HN1202-R strain by intranasal instillation, respectively, and another five piglets were used as the blank control group; a group (5) of piglets at 7 days of age which were negative for pseudorabies antigens and antibodies were inoculated with 1 ml ($10^{7.0}$ $TCID_{50}$/ml) of the cultures of the $1^{st}$, $30^{th}$, $85^{th}$ and $110^{th}$ passages of PRV Fa-R strain by intranasal instillation, respectively, and another five piglets were used as the control group. The clinical manifestations of piglets were observed and recorded daily until 28 days after inoculation of virus.

It showed in the results that, from the observation of piglets for 28 days after inoculation with the cultures of the $1^{st}$, $30^{th}$, $60^{th}$, $85^{th}$ and $110^{th}$ passages of PRV HN1202-R strain, PRV HN1202-R strain displayed a significant reduction of virulence, only causing increased body temperature of 2~3 pigs/group, without any other clinical signs, or any changes of tissues or organs obtained from the necropsy; from the observation of piglets for 28 days after inoculation with the cultures of the $1^{st}$, $30^{th}$, $60^{th}$, $85^{th}$ and $110^{th}$ passages of PRV HN1202-R strain, PRV Fa-R strain displayed a significant reduction of virulence, only causing increased body temperature of 3-4 pigs/group, without any other clinical signs, or any changes of tissues or organs obtained from the necropsy.

Through the pathogenicity test of different passages, it indicated that different passages of PRV HN1202-R strain and Fa-R strain all displayed lower virulence.

2. Immunogenicity Assay

On the $21^{st}$ day after immunization, all the five piglets inoculated with PRV 1202-R strain and five piglets in the control group were challenged with $1\times10^{7.0}$ $TCID_{50}$/piglet of PRV 1202 strain. After challenge, the body temperature of piglets was measured daily, and in the meanwhile clinical signs and death status were observed. The results are shown in Table 9.

On the $21^{st}$ day after immunization, all the five piglets inoculated with PRV Fa-R strain and five piglets in the control group were challenged with $1\times10^{7.0}$ $TCID_{50}$/piglet of PRV Fa strain. After challenge, the body temperature of piglets was measured daily, and in the meanwhile clinical signs and death status were observed. The results are shown in Table 9.

TABLE 9

Pathogenicity of HN1202-R strain and Fa-R strain in 7-day-old piglets

| Group | Number | Clinical signs and death status | Protection Rate |
|---|---|---|---|
| C | C1 | Normal body temperature, normal appetite, no abnormal clinical signs, survived | 100% (5/5) |
| | C2 | Normal body temperature, normal appetite, no abnormal clinical signs, survived | |
| | C3 | Normal body temperature, normal appetite, no abnormal clinical signs, survived | |
| | C4 | Normal body temperature, normal appetite, no abnormal clinical signs, survived | |
| | C5 | Normal body temperature, normal appetite, no abnormal clinical signs, survived | |
| Blank control | K6 | Body temperature increased, depression, loss of appetite, significant clinical signs, died on day 4 after challenge | 0% (0/5) |
| | K7 | Body temperature increased, depression, complete loss of appetite, significant clinical signs, died on day 5 after challenge | |
| | K8 | Body temperature increased, depression, complete loss of appetite, significant clinical signs, died on day 5 after challenge | |
| | K9 | Body temperature increased, depression, loss of appetite, significant clinical signs, died on day 4 after challenge | |
| | K10 | Body temperature increased, depression, loss of appetite, significant clinical signs, died on day 4 after challenge | |
| E | E1 | Normal body temperature, normal appetite, no abnormal clinical signs, survived | 100% (5/5) |
| | E2 | Normal body temperature, normal appetite, no abnormal clinical signs, survived | |
| | E3 | Normal body temperature, normal appetite, no abnormal clinical signs, survived | |
| | E4 | Normal body temperature, normal appetite, no abnormal clinical signs, survived | |
| | E5 | Normal body temperature, normal appetite, no abnormal clinical signs, survived | |
| Blank control | K11 | Body temperature increased, depression, loss of appetite, significant clinical signs, died on day 5 after challenge | 0% (0/5) |
| | K12 | Body temperature increased, depression, complete loss of appetite, significant clinical signs, died on day 4 after challenge | |
| | K13 | Body temperature increased, depression, complete loss of appetite, significant clinical signs, died on day 4 after challenge | |
| | K14 | Body temperature increased, depression, loss of appetite, significant clinical signs, died on day 5 after challenge | |
| | K15 | Body temperature increased, depression, loss of appetite, significant clinical signs, died on day 5 after challenge | |

The result indicated that all the piglets inoculated with PRV HN1202-R strain were healthy and alive, while all from the control group died; all the piglets inoculated with PRV Fa-R strain were healthy and alive, while all from the control group died.

According to the immunogenicity assay, the PRV HN1202-R strain can provide excellent protection against PRV HN1202 strain, showing excellent immunogenicity;

the PRV Fa-R strain can provide excellent protection against PRV Fa strain, showing excellent immunogenicity.

Meanwhile, in order to verify the stability of immunogenicity of different passages of PRV HN1202-R strain and Fa-R strain, on the $21^{st}$ day after immunization, all the immune groups inoculated with the cultures of the $1^{st}$, $30^{th}$, $60^{th}$, $85^{th}$ and $110^{th}$ passages of PRV HN1202-R strain as well as the control group were challenged with $1\times10^{7.0}$ $TCID_{50}$/piglet of PRV HN1202; after challenge, the body temperature of piglets was measured daily, and in the meanwhile clinical signs and death status were observed; on the $21^{st}$ day after immunization, all the immune groups inoculated with the cultures of the $1^{st}$, $30^{th}$, $60^{th}$, $85^{th}$ and $110^{th}$ passages of PRV Fa-R strain as well as the control group were challenged with $1\times10^{7.0}$ $TCID_{50}$/piglet of PRV Fa. After challenge, the body temperature of piglets was determined daily, and in the meanwhile clinical signs and death status were observed.

The result indicated that all the piglets inoculated with the cultures of the $1^{st}$, $30^{th}$, $60^{th}$, $85^{th}$ and $110^{th}$ passages of PRV HN1202-R strain were healthy and alive, while all from the control group died; all the piglets inoculated with the cultures of the $1^{st}$, $30^{th}$, $60^{th}$, $85^{th}$ and $110^{th}$ passages of PRV Fa-R strain were healthy and alive, while all from the control group died.

According to the immunogenicity assay of different passages, the culture of different passages of PRV HN1202-R strain all can provide excellent protection against PRV HN1202 strain, showing excellent immunogenicity; the culture of different passages of PRV Fa-R strain all can provide excellent protection against PRV Fa strain, showing excellent immunogenicity.

3. Reversion of Virulence Test of the Virus 30 piglets at 7 days of age which were negative for pseudorabies antigens and antibodies were randomly divided into 5 groups, each with 6 piglets. 6 piglets of Group 1 which were negative for pseudorabies antigens and antibodies were inoculated with $10^{7.0}$ $TCID_{50}$/piglet of the cultures of PRV HN1202-R (the $1^{st}$, $30^{th}$, $60^{th}$, $85^{th}$, $110^{th}$ passages and the $1^{st}+30^{th}+60^{th}+85^{th}+110^{th}$ passages) respectively by intranasal instillation. On day 14, they were raised together with the 6 piglets of Group 2 which were negative for pseudorabies antigens and antibodies. 14 days later, the 6 piglets of Group 1 were drawn back, and again, the 6 piglets of Group 3, which were negative for pseudorabies antigens and antibodies, were raised together with the 6 piglets of Group 2 and so on. After 4 continuous passages, all the drawn piglets were killed in order to observe if there were any pathological changes.

It showed in the result that no abnormal changes were found during the clinical observation and gross anatomy of 30 experimental piglets infected with HN1202-R strain and 30 experimental piglets infected with Fa-R strain, by the 4th serial passage of the cohabitation infection experiment, indicating that there was no reversion of virulence of the two attenuated strains. Therefore, the safety of the vaccines can be ensured since the viruses, after being inoculated into piglets, would not evolve into virulent viruses which are able to cause disease.

4. Gene Sequences Analysis

The genome amplification of the cultures of the $1^{st}$ passage to $110^{th}$ passage of PRV HN1202-R strain was accomplished by means of RT-PCR (The genomic DNA of culture of different passages was amplified respectively). The product acquired from amplification was recovered, purified, and linked to the plasmid vector for sequencing, so that the nucleotide sequence of the viral gene was determined and transformed through computer software into the amino acid sequence of the virus. The obtained amino acid sequence was compared with the amino acid sequence of the parent virulent strain, i.e. PRV HN1202 strain via sequence analysis software, and the amino acids sequence of the virus was characterized.

Meanwhile, the genome amplification of the cultures of the $1^{st}$ passage to $110^{th}$ passage of PRV Fa-R strain was accomplished by means of RT-PCR (The genomic DNA of culture of different passages was amplified respectively). The product acquired from amplification was recovered, purified, and linked to the plasmid vector for sequencing, so that the nucleotide sequence of the viral gene was determined and transformed through computer software into the amino acid sequence of the virus. The obtained amino acid sequence was compared with the amino acid sequence of the parent virulent strain, PRV Fa strain via software for sequence analysis, and the amino acids sequence of the virus was characterized.

It showed in the results that for the cultures of the $1^{st}$ passage to $110^{th}$ passage of PRV HN1202-R strain, the amino acids sequences encoded by each viral genes commonly have continuous deficiency of gI/gE/11K/28K genes (3455 bp in total), in which the deficiency site and size are totally the same as those of PRV HN1201-R strain; for the cultures of the $1^{st}$ passage to $110^{th}$ passage of PRV Fa-R strain, the amino acids sequences encoded by each viral genes commonly have continuous deficiency of gI/gE/11K/28K genes (3455 bp in total), in which the deficiency site and size are totally the same as those of PRV HN1201-R strain; compared with their parent virulent strains, each of PRV HN1202-R strain and PRV Fa-R strain has continuous deficiency of gI/gE/11K/28K genes (3455 bp in total).

It indicated that a common characteristic change of the amino acids sequences encoded by the viral genes of the cultures of the different passages of PRV HN1202-R strain as well as PRV Fa-R strain is consistent with that of the amino acids encoded by the viral genes of PRV HN1201-R strain, which is caused by the deficiency of genes encoding said amino acids sequences, showing the stability of the method of attenuating the PRV by passage according to the present invention, and in the meanwhile, further indicating that continuous deficiency of gI/gE/11K/28K genes (3455 bp in total) in PRV is the reason for the reduction of virulence of its parent virulent strain.

Example 8: Preparation of the Attenuated Live Vaccines of PRV HN1202-R Strain and Fa-R Strain The attenuated live vaccines of PRV HN1202-R strain and Fa-R strain were prepared according to the procedure in Example 3. The specific ratios of contents of the vaccines are shown in Table 10.

TABLE 10 ratios of contents of the attenuated live vaccines of PRV HN1202-R strain and Fa-R strain

| | Antigen ($TCID_{50}$) | protective agent (V/V) |
|---|---|---|
| Vaccine 3 (HN1202-R strain) | $10^{6.0}$ | 50% |
| Vaccine 4 (Fa-R strain) | $10^{6.0}$ | 50% |

Example 9: Immunogenicity Assay of the Attenuated Live Vaccine of PRV HN1202-R Strain and Fa-R Strain 20 9-day-old piglets which were negative for PRV antigens and antibodies and PRV antigens were randomly divided into 4 groups, each with 5 piglets, and the piglets were injected with the attenuated live vaccine of PRV HN1202-R strain and Fa-R strain prepared in Example 8. The first group was immunized with Vaccine 3, and the third group was immunized with Vaccine 4, and the second and fourth group was the control group. The piglets in the first and second groups were challenged with $1\times10^{7.0}$ $TCID_{50}$/piglet of PRV HN1202 strain on day 21 after immunization, and those in the third and fourth groups were challenged with $1\times10^{7.0}$ $TCID_{50}$/piglet of PRV Fa strain. After challenge, the body temperature of piglets was measured daily, and in the meanwhile clinical signs and death status were observed. The specific results are shown in Table 11.

TABLE 11

Results of immunogenicity assay of the attenuated live vaccine of HN1202-R strain and Fa-R strain

| Group | Number of piglets | Dose of Challenge | Clinical signs and death status | Rate of protection |
|---|---|---|---|---|
| Vaccine 3 | 5 | $10^{7.0}TCID_{50}$/piglet of HN1202 strain | Normal body temperature, normal appetite, no abnormal clinical signs, survived | 100% (5/5) |
| Control vaccine | 5 | $10^{7.0}TCID_{50}$/piglet of HN1202 strain | All the pigs displayed symptoms like increased body temperature, depression, complete or partial loss of appetite, and significant clinical signs; four died on day 4 after challenge, and all died within 5 days after challenge. | 0% (0/5) |
| Vaccine 4 | 5 | $10^{7.0}TCID_{50}$/piglet of Fa strain | Normal body temperature, normal appetite, no abnormal clinical signs, survived | 100% (5/5) |
| Control vaccine | 5 | $10^{7.0}TCID_{50}$/piglet of Fa strain | All the pigs displayed symptoms like increased body temperature, depression, complete or partial loss of appetite, and significant clinical signs; two died on day 4 after challenge, and all died within 4 days after challenge. | 0% (0/5) |

The result indicated that immunizing piglets with the attenuated live vaccine of PRV HN1202-R strain prepared in example 8 can block virus infection (i.e. prevent occurrence of clinical signs), and provide 100% (5/5) protection rate for piglets, while all the piglets in the blank control group died by day 5 after challenge; immunizing piglets with the attenuated live vaccine of PRV Fa-R strain prepared in example 8 can block virus infection (i.e. prevent occurrence of clinical signs), and provide 100% (5/5) protection rate for piglets, while all the piglets in the blank control group died by day 5 after challenge.

It has proven that the attenuated live vaccines of PRV HN1202-R strain and Fa-R strain can provide excellent protection, showing excellent immune protection and safety; meanwhile it indicated again that a continuous deficiency of gI/gE/11K/28K genes (3455 bp in total) from the PRV virus would have no effect on its immunogenicity.

Example 10: Construction of PRV HN1201-$gI^-$/$gE^-$/$11K^-$/$28K^-$ Gene-Deleted Strain In order to obtain the PRV HN1201-$gI^-$/$gE^-$/$11K^-$/$28K^-$ gene-deleted strain, the gI/gE/11K/28K genes were knocked out through molecular cloning by means of homologous recombination. The detailed procedures are as follows:

The sequence at the front end of US7 and the sequence at the back section of US2 were amplified respectively, as the left and right homologous recombinant arms US7L and US2R, with the genomic DNA of PRV HN1201 strain as the template, and US7-LP1/US7-LP2 and US2-RP1/US2-RP2 as the primers, in which there is a loxP site at each end of gIL and US2R. The transfer vector, pSKUS7-2-GFP with the loxP sites was constructed by use of pBluescript SK plasmid, with the green fluorescent protein GFP as the selectable marker.

The total DNA of PK-15 cells infected by PRV HN1201 strain was extracted via the DNAZol method, and the total DNA and the transfer vector, pSKUS7-2-GFP was co-transfected at the ratio of 10 μg:1 μg, into the PK-15 cells via the lipofectin-mediated transfection. The viruses were harvested when the cytopathic effect of cells reached 80%. After serial dilution, the harvested viruses were inoculated into a monolayer of PK-15 cells, to obtain the recombinant virus rPRV-US7-$2^-$/$GFP^+$ with GFP by means of plaque purification. 10 μg of the DNA of rPRV-US7-$2^-$/$GFP^+$ was added with 2.5 units of Cre recombinase and reacted for 1 h at 37° C.; the DNA was extracted to prepare DNA of rPRV-US7-$2^-$, which was then transfected into PK-15 cells. After plaques purification, the gene-deleted PRV strain containing no GFP, PRV HN1201-$gI^-$/$gE^-$/$11K^-$/$28K^-$ gene-deleted strain was obtained.

Example 11: Preparation of the Attenuated Live Vaccines of PRV HN1201-$gI^-$/$gE^-$/$11K^-$/$28K^-$ Gene-Deleted Strain The attenuated live vaccines of PRV HN1201-$gI^-$/$gE^-$/$11K^-$/$28K^-$ gene-deleted strain were prepared according to the procedure in Example 3. The specific ratios of content of the vaccine are shown in Table 12.

TABLE 12 ratios of contents of the attenuated live vaccines of PRV HN1201-$gI^-$/$gE^-$/$11K^-$/$28K^-$ gene-deleted strain

| | Antigen ($TCID_{50}$) | protective agent (V/V) |
|---|---|---|
| Vaccine 5 (HN1201-$gI^-$/$gE^-$/$11K^-$/$28K^-$) | $10^{6.0}$ | 50% |

10 9-day-old piglets which were negative for PRV antigens and antibodies were randomly divided into 2 groups, each with 5 piglets, and the piglets were immunized with the attenuated live vaccine of PRV HN1201-$gI^-$/$gE^-$/$11K^-$/$28K^-$ strain. The piglets were challenged with $1\times10^{7.0}$ $TCID_{50}$/piglet of PRV HN1201 strain on day 21 after immunization. After challenge, the body temperature of piglets was measured daily, and in the meanwhile clinical signs and death status were observed. The detailed results are shown in Table 13.

TABLE 13

Results of Immunogenicity assay of the attenuated live vaccine of HN1201-$gI^-$/$gE^-$/$11K^-$/$28K^-$ strain

| Group | Number of piglets | Dose of Challenge | Clinical signs and death status | Rate of protection |
|---|---|---|---|---|
| Vaccine 5 | 5 | $10^{7.0}$$TCID_{50}$/piglet of HN1201 strain | Normal body temperature, normal appetite, no abnormal clinical signs, survived | 80% (4/5) |
| Control vaccine | 5 | $10^{7.0}$$TCID_{50}$/piglet of HN1201 strain | All the pigs displayed symptoms like increased body temperature, depression, complete or partial loss of appetite, and significant clinical signs; two died on day 3 after challenge, and all died within 4 days after challenge. | 0% (0/5) |

The results indicated that immunizing piglets with the attenuated live vaccine of PRV HN1201-$gI^-$/$gE^-$/$11K^-$/$28K^-$ strain prepared by means of genetic engineering can block virus infection (i.e. prevent occurrence of clinical signs), and provide 80% (4/5) protection rate for piglets, while all the piglets in the blank control group died by day 4 after challenge.

It has proven that the attenuated live vaccine of PRV HN1201-$gI^-$/$gE^-$/$11K^-$/$28K^-$ strain can provide excellent protection, showing excellent immune protection and safety; meanwhile it indicated again that a continuous deficiency of gI/gE/11K/28K genes (3455 bp in total) from the PRV virus would have no effect on its immunogenicity.

Example 12: Acquisition of PRV PRV-ZJ01-R Strain, HeN1-R Strain and JS-2012-R Strain PRV PRV-ZJ01 strain, HeN1 strain and JS-2012 strain were subcultured to be attenuated respectively according to the procedures in Example 1, in order to obtain their attenuated PRV strains, named PRV-ZJ01-R strain, HeN1-R strain and JS-2012-R strain.

Example 13: Study of Biological Characteristics of PRV-ZJ01-R Strain, PRV HeN1-R Strain and PRV JS-2012-R Strain 1. Pathogenicity Test of the Virus 30 piglets at 7 days of age which were negative for pseudorabies antigens and antibodies were randomly divided into 6 groups (G, H, I, J, L and M), each with 5 piglets; another 15 piglets were used as the blank control group. The grouping and challenging conditions are shown in Table 14.

TABLE 14

Grouping of the animals in the pathogenicity test for PRV-ZJ01-R strain, HeN1-R strain and JS-2012-R strain

| Group | Strains used for inoculation | Dose of inoculation |
|---|---|---|
| G | PRV-ZJ01-R strain | inoculated with 1 ml ($10^{7.0}$ $TCID_{50}$/ml)/piglet by intranasal instillation |
| H | PRV-ZJ01 strain | inoculated with 1 ml ($10^{7.0}$ $TCID_{50}$/ml)/piglet by intranasal instillation |
| I | HeN1-R strain | inoculated with 1 ml ($10^{7.0}$ $TCID_{50}$/ml)/piglet by intranasal instillation |
| J | HeN1 strain | inoculated with 1 ml ($10^{7.0}$ $TCID_{50}$/ml)/piglet by intranasal instillation |
| L | JS-2012-R strain | inoculated with 1 ml ($10^{7.0}$ $TCID_{50}$/ml)/piglet by intranasal instillation |
| M | JS-2012 strain | inoculated with 1 ml ($10^{7.0}$ $TCID_{50}$/ml)/piglet by intranasal instillation |
| Blank control | DMEM medium | inoculated with 1 ml/piglet by intranasal instillation |

Piglets were observed for 28 days after inoculation of virus, while the temperature of piglets was measured daily, and clinical signs and death status were observed. The specific results are shown in Table 15.

TABLE 15

Pathogenicity of PRV-ZJ01-R strain, HeN1-R strain and JS-2012-R strain in 7-day-old piglets

| Group | Number | Clinical signs | Death status |
|---|---|---|---|
| G | G1 | Body temperature increased for 1 day, no other clinical signs | Survived |
| | G2 | Body temperature increased for 1 day, no other clinical signs | Survived |
| | G3 | Body temperature increased for 1 day, no other clinical signs | Survived |
| | G4 | Normal body temperature, no clinical signs | Survived |
| | G5 | Body temperature increased for 1 day, no other clinical signs | Survived |
| H | H1 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | H2 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | H3 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | H4 | Body temperature increased for 5 days, depression, complete loss of appetite, remaining recumbent, dyspnea, trembling; neurological signs such as convulsions, turning around, and making strokes with their forelimbs, etc. | Died on day 5 after challenge |

TABLE 15-continued

Pathogenicity of PRV-ZJ01-R strain, HeN1-R strain and JS-2012-R strain in 7-day-old piglets

| Group | Number | Clinical signs | Death status |
|---|---|---|---|
| | H5 | Body temperature increased for 5 days, depression, complete loss of appetite, remaining recumbent, dyspnea, trembling; neurological signs such as convulsions, turning around, and making strokes with their forelimbs, etc. | Died on day 5 after challenge |
| I | I1 | Body temperature increased for 1 day, no other clinical signs | Survived |
| | I2 | Body temperature increased for 1 day, no other clinical signs | Survived |
| | I3 | Normal body temperature, no clinical signs | Survived |
| | I4 | Body temperature increased for 1 day, no other clinical signs | Survived |
| | I5 | Body temperature increased for 1 day, no other clinical signs | Survived |
| J | J1 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | J2 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | J3 | Body temperature increased for 5 days, depression, complete loss of appetite, remaining recumbent, dyspnea, trembling; neurological signs such as convulsions, turning around, and making strokes with their forelimbs, etc. | Died on day 5 after challenge |
| | J4 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | J5 | Body temperature increased for 5 days, depression, complete loss of appetite, remaining recumbent, dyspnea, trembling; neurological signs such as convulsions, turning around, and making strokes with their forelimbs, etc. | Died on day 5 after challenge |
| L | L1 | Normal body temperature, no clinical signs | Survived |
| | L2 | Body temperature increased for 1 day, no other clinical signs | Survived |
| | L3 | Body temperature increased for 1 day, no other clinical signs | Survived |
| | L4 | Body temperature increased for 1 day, no other clinical signs | Survived |
| | L5 | Body temperature increased for 1 day, no other clinical signs | Survived |
| M | M1 | Body temperature increased for 5 days, depression, complete loss of appetite, remaining recumbent, dyspnea, trembling; neurological signs such as convulsions, turning around, and making strokes with their forelimbs, etc. | Died on day 5 after challenge |
| | M2 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | M3 | Body temperature increased for 5 days, depression, complete loss of appetite, remaining recumbent, dyspnea, trembling; neurological signs such as convulsions, turning around, and making strokes with their forelimbs, etc. | Died on day 5 after challenge |
| | M4 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| | M5 | Body temperature increased for 4 days, depression, complete loss of appetite, remaining recumbent, dyspnea, trembling; neurological signs such as convulsions, turning around, and making strokes with their forelimbs, etc. | Died on day 4 after challenge |
| Blank control | K16 | no abnormal clinical signs | Survived |
| | K17 | no abnormal clinical signs | Survived |
| | K18 | no abnormal clinical signs | Survived |
| | K19 | no abnormal clinical signs | Survived |
| | K20 | no abnormal clinical signs | Survived |
| | K21 | no abnormal clinical signs | Survived |
| | K22 | no abnormal clinical signs | Survived |
| | K23 | no abnormal clinical signs | Survived |
| | K24 | no abnormal clinical signs | Survived |
| | K25 | no abnormal clinical signs | Survived |
| | K26 | no abnormal clinical signs | Survived |
| | K27 | no abnormal clinical signs | Survived |
| | K28 | no abnormal clinical signs | Survived |
| | K29 | no abnormal clinical signs | Survived |
| | K30 | no abnormal clinical signs | Survived |

It showed in the results that inoculation with PRV PRV-ZJ01 strain into 7-day-old piglets could lead to death of 100% (5/5) of inoculated piglets, while PRV PRV-ZJ01-R strain displayed a significant reduction of virulence, only causing increased body temperature of four pigs, without any other clinical signs, or any changes of tissues or organs obtained from the necropsy; inoculation with PRV HeN1 strain into 7-day-old piglets could lead to death of 100% (5/5) of inoculated piglets, while PRV HeN1-R strain displayed a significant reduction of virulence, only causing increased body temperature of four pigs, without any other clinical signs, or any changes of tissues or organs obtained from the necropsy; inoculation with PRV JS-2012 strain into 7-day-old piglets could lead to death of 100% (5/5) of inoculated piglets, while PRV JS-2012-R strain displayed a significant reduction of virulence, only causing increased body temperature of four pigs, without any other clinical signs, or any changes of tissues or organs obtained from the necropsy.

Through the pathogenicity test it indicated that compared with the parent virulent strain, i.e. PRV PRV-ZJ01 strain, PRV-ZJ01-R strain displayed a significant reduction of pathogenicity, and was an attenuated virus strain; compared with the parent virulent strain, i.e. PRV HeN1 strain, PRV HeN1-R strain displayed a significant reduction of pathogenicity, and was an attenuated virus strain; compared with the parent virulent strain, i.e. PRV JS-2012 strain, PRV JS-2012-R strain displayed a significant reduction of pathogenicity, and was an attenuated virus strain.

Meanwhile, in order to verify the stability of pathogenicity of different passages of PRV PRV-ZJ01-R strain, PRV HeN1-R strain and PRV JS-2012-R strain, a group of piglets (5 piglets) at 7 days of age which were negative for pseudorabies antigens and antibodies were inoculated with 1 ml ($10^{7.0}$ $TCID_{50}$/ml) of the cultures of the $1^{st}$, $30^{th}$, $60^{th}$, $85^{th}$ and $110^{th}$ passages of PRV PRV-ZJ01-R strain by intranasal instillation, respectively, and another five piglets were used as the blank control group; a group of piglets (5 piglets) at 7 days of age which were negative for pseudorabies antigens and antibodies were inoculated with 1 ml ($10^{7.0}$ $TCID_{50}$/ml) of the cultures of the $1^{st}$, $30^{th}$, $60^{th}$, $85^{th}$ and $110^{th}$ passages of PRV HeN1-R strain by intranasal instillation, respectively, and another five piglets were used as the blank control group; a group of piglets (5 piglets) at 7 days of age which were negative for pseudorabies antigens and antibodies were inoculated with 1 ml ($10^{7.0}$ $TCID_{50}$/ml) of the cultures of the $1^{st}$, $30^{th}$, $60^{th}$, $85^{th}$ and $110^{th}$ passages of PRV JS-2012-R strain by intranasal instillation, respectively, and another five piglets were used as the control group. The clinical manifestations of piglets were observed and recorded daily until 28 days after inoculation of virus.

It showed in the results that, from the observation of piglets for 28 days after inoculation with the cultures of the $1^{st}$, $30^{th}$, $60^{th}$, $85^{th}$ and $110^{th}$ passages of PRV PRV-ZJ01-R strain, PRV PRV-ZJ01-R strain displayed a significant reduction of virulence, only causing increased body temperature of 4~5 pigs/group, without any other clinical signs, or any changes of tissues or organs obtained from the necropsy; from the observation of piglets for 28 days after inoculation with the cultures of the $1^{st}$, $30^{th}$, $60^{th}$, $85^{th}$ and $110^{th}$ passages of PRV HeN1-R strain, PRV HeN1-R strain displayed a significant reduction of virulence, only causing increased body temperature of 4~5 pigs/group, without any other clinical signs, or any changes of tissues or organs obtained from the necropsy; from the observation of piglets for 28 days after inoculation with the cultures of the $1^{st}$, $30^{th}$, $60^{th}$, $85^{th}$ and $110^{th}$ passages of PRV JS-2012-R strain, PRV JS-2012-R strain displayed a significant reduction of virulence, only causing increased body temperature of 4~5 pigs/group, without any other clinical signs, or any changes of tissues or organs obtained from the necropsy.

Through the pathogenicity test of different passages, it indicated that different passages of PRV PRV-ZJ01-R strain, HeN1-R strain and PRV JS-2012-R strain all displayed lower virulence.

2. Immunogenicity Assay

On the $21^4$ day after immunization, all the five piglets inoculated with PRV PRV-ZJ01-R strain and five piglets in the control group were challenged with $1\times10^{7.0}$ $TCID_{50}$/piglet of PRV PRV-ZJ01 strain. After challenge, the body temperature of piglets was measured daily, and in the meanwhile clinical signs and death status were observed. The results are shown in Table 16.

On the $21^4$ day after immunization, all the five piglets inoculated with PRV HeN1-R strain and five piglets in the control group were challenged with $1\times10^{7.0}$ $TCID_{50}$/piglet of PRV HeN1 strain. After challenge, the body temperature of piglets was measured daily, and in the meanwhile clinical signs and death status were observed. The results are shown in Table 16.

On the $21^4$ day after immunization, all the five piglets inoculated with PRV JS-2012-R strain and five piglets in the control group were challenged with $1\times10^{7.0}$ $TCID_{50}$/piglet of PRV JS-2012 strain. After challenge, the body temperature of piglets was measured daily, and in the meanwhile clinical signs and death status were observed. The results are shown in Table 16.

TABLE 16

Pathogenicity of PRV-ZJ01-R strain, PRV HeN1-R strain and PRV JS-2012-R strain in 7-day-old piglets

| Group | Number | Clinical signs and death status | Protection rate |
|---|---|---|---|
| G | G1 | Normal body temperature, normal appetite, no abnormal clinical signs, survived | 100% (5/5) |
| | G2 | Normal body temperature, normal appetite, no abnormal clinical signs, survived | |
| | G3 | Normal body temperature, normal appetite, no abnormal clinical signs, survived | |
| | G4 | Normal body temperature, normal appetite, no abnormal clinical signs, survived | |
| | G5 | Normal body temperature, normal appetite, no abnormal clinical signs, survived | |
| Blank control | K16 | Body temperature increased, depression, loss of appetite, significant clinical signs, died on day 4 after challenge | 0% (0/5) |
| | K17 | Body temperature increased, depression, complete loss of appetite, significant clinical signs, died on day 5 after challenge | |
| | K18 | Body temperature increased, depression, complete loss of appetite, significant clinical signs, died on day 5 after challenge | |
| | K19 | Body temperature increased, depression, loss of appetite, significant clinical signs, died on day 5 after challenge | |
| | K20 | Body temperature increased, depression, loss of appetite, significant clinical signs, died on day 4 after challenge | |
| I | I1 | Normal body temperature, normal appetite, no abnormal clinical signs, survived | 100% (5/5) |
| | I2 | Normal body temperature, normal appetite, no abnormal clinical signs, survived | |
| | I3 | Normal body temperature, normal appetite, no abnormal clinical signs, survived | |
| | I4 | Normal body temperature, normal appetite, no abnormal clinical signs, survived | |
| | I5 | Normal body temperature, normal appetite, no abnormal clinical signs, survived | |
| Blank control | K21 | Body temperature increased, depression, loss of appetite, significant clinical signs, died on day 5 after challenge | 0% (0/5) |
| | K22 | Body temperature increased, depression, complete loss of appetite, significant clinical signs, died on day 4 after challenge | |
| | K23 | Body temperature increased, depression, complete loss of appetite, significant clinical signs, died on day 4 after challenge | |
| | K24 | Body temperature increased, depression, loss of appetite, significant clinical signs, died on day 5 after challenge | |
| | K25 | Body temperature increased, depression, loss of appetite, significant clinical signs, died on day 5 after challenge | |
| L | L1 | Normal body temperature, normal appetite, no abnormal clinical signs, survived | 100% (5/5) |
| | L2 | Normal body temperature, normal appetite, no abnormal clinical signs, survived | |
| | L3 | Normal body temperature, normal appetite, no abnormal clinical signs, survived | |
| | L4 | Normal body temperature, normal appetite, no abnormal clinical signs, survived | |
| | L5 | Normal body temperature, normal appetite, no abnormal clinical signs, survived | |

TABLE 16-continued

Pathogenicity of PRV-ZJ01-R strain, PRV HeN1-R strain and PRV JS-2012-R strain in 7-day-old piglets

| Group | Number | Clinical signs and death status | Protection rate |
|---|---|---|---|
| Blank control | K26 | Body temperature increased, depression, loss of appetite, significant clinical signs, died on day 5 after challenge | 0% (0/5) |
| | K27 | Body temperature increased, depression, complete loss of appetite, significant clinical signs, died on day 4 after challenge | |
| | K28 | Body temperature increased, depression, complete loss of appetite, significant clinical signs, died on day 4 after challenge | |
| | K29 | Body temperature increased, depression, loss of appetite, significant clinical signs, died on day 5 after challenge | |
| | K30 | Body temperature increased, depression, loss of appetite, significant clinical signs, died on day 5 after challenge | |

The results indicated that all the piglets inoculated with PRV PRV-ZJ01-R strain were healthy and alive, while all from the control group died; all the piglets inoculated with PRV HeN1-R strain were healthy and alive, while all from the control group died; all the piglets inoculated with PRV JS-2012-R strain were healthy and alive, while all from the control group died.

According to the immunogenicity assay, the PRV PRV-ZJ01-R strain can provide excellent protection against PRV PRV-ZJ01 strain, showing excellent immunogenicity; the PRV HeN1-R strain can provide excellent protection against PRV HeN1 strain, showing excellent immunogenicity; the PRV JS-2012-R strain can provide excellent protection against PRV JS-2012 strain, showing excellent immunogenicity.

Meanwhile, in order to verify the stability of immunogenicity of different passages of PRV PRV-ZJ01-R strain, PRV HeN1-R strain and PRV JS-2012-R strain, on the $21^{st}$ day after immunization, all the immune groups inoculated with the cultures of the $1^{st}$, $30^{th}$, $60^{th}$, $85^{th}$ and $110^{th}$ passages of PRV PRV-ZJ01-R strain as well as the control group were challenged with $1\times10^{7.0}$ $TCID_{50}$/piglet of PRV PRV-ZJ01 strain; after challenge, the body temperature of piglets was measured daily, and in the meanwhile clinical signs and death status were observed; on the $21^{st}$ day after immunization, all the immune groups inoculated with the cultures of the $1^{st}$, $30^{th}$, $60^{th}$, $85^{th}$ and $110^{th}$ passages of PRV HeN1-R strain as well as the control group were challenged with $1\times10^{7.0}$ $TCID_{50}$/piglet of PRV HeN1 strain; after challenge, the body temperature of piglets was measured daily, and in the meanwhile clinical signs and death status were observed; on the $21^{st}$ day after immunization, all the immune groups inoculated with the cultures of the $1^{st}$, $30^{th}$, $60^{th}$, $85^{th}$ and $110^{th}$ passages of PRV JS-2012-R strain as well as the control group were challenged with $1\times10^{7.0}$ $TCID_{50}$/piglet of PRV JS-2012 strain. After challenge, the body temperature of piglets was measured daily, and in the meanwhile clinical signs and death status were observed.

The result indicated that all the piglets inoculated with the cultures of the $1^{st}$, $30^{th}$, $60^{th}$, $85^{th}$ and $110^{th}$ passages of PRV PRV-ZJ01-R strain were healthy and alive, while all from the control group died; all the piglets inoculated with the cultures of the $1^{st}$, $30^{th}$, $60^{th}$, $85^{th}$ and $110^{th}$ passages of PRV HeN1-R strain were healthy and alive, while all from the control group died; all the piglets inoculated with the cultures of the $1^{st}$, $30^{th}$, $60^{th}$, $85^{th}$ and $110^{th}$ passages of PRV JS-2012-R strain were healthy and alive, while all from the control group died.

According to the immunogenicity assay of different passages, the culture of different passages of PRV PRV-ZJ01-R strain all can provide excellent protection against PRV PRV-ZJ01 strain, showing excellent immunogenicity; the culture of different passages of PRV HeN1-R strain all can provide excellent protection against PRV HeN1 strain, showing excellent immunogenicity; the culture of different passages of PRV JS-2012-R strain all can provide excellent protection against PRV JS-2012 strain, showing excellent immunogenicity.

3. Reversion of Virulence Test of the Virus 30 piglets at 7 days of age which were negative for pseudorabies antigens and antibodies were randomly divided into 5 groups, each with 6 piglets. 6 piglets of Group 1 which were negative for pseudorabies antigens and antibodies were inoculated with $10^{7.0}$ $TCID_{50}$/piglet of the cultures of PRV PRV-ZJ01-R strain (the $1^{st}$, $30^{th}$, $60^{th}$, $85^{th}$, $110^{th}$ passages and the $1^{st}$+$30^{th}$+$60^{th}$+$85^{th}$+$110^{th}$ passages) respectively by intranasal instillation. On day 14, they were raised together with the 6 piglets of Group 2 which were negative for pseudorabies antigens and antibodies. 14 days later, the 6 piglets of Group 1 were drawn back, and again, the 6 piglets of Group 3, which were negative for pseudorabies antigens and antibodies, were raised together with the 6 piglets of Group 2, and so on. After 4 serial passages, all the drawn piglets were killed in order to observe if there were any pathological changes.

30 piglets at 7 days of age which were negative for pseudorabies antigens and antibodies were randomly divided into 5 groups, each with 6 piglets. 6 piglets of Group 1 which were negative for pseudorabies antigens and antibodies were inoculated with $10^{7.0}$ $TCID_{50}$/piglet of the cultures of PRV HeN1-R strain (the $1^{st}$, $30^{th}$, $60^{th}$, $85^{th}$, $110^{th}$ passages and the $1^{st}$+$30^{th}$+$60^{th}$+$85^{th}$+$110^{th}$ passages) respectively by intranasal instillation. On day 14, they were raised together with the 6 piglets of Group 2 which were negative for pseudorabies antigens and antibodies. 14 days later, the 6 piglets of Group 1 were drawn back, and again, the 6 piglets of Group 3 which were negative for pseudorabies antigens and antibodies, were raised together with the 6 piglets of Group 2, and so on. After 4 serial passages, all the drawn piglets were killed in order to observe if there are any pathological changes.

30 piglets at 7 days of age which were negative for pseudorabies antigens and antibodies were randomly divided into 5 groups, each with 6 piglets. 6 piglets of Group 1 which were negative for pseudorabies antigens and antibodies were inoculated with $10^{7.0}$ $TCID_{50}$/piglet of the cultures of PRV JS-2012-R strain (the $1^{st}$, $30^{th}$, $60^{th}$, $85^{th}$, $110^{th}$ passages and the $1^{st}$+$30^{th}$+$60^{th}$+$85^{th}$+$110^{th}$ passages) respectively by intranasal instillation. On day 14, they were raised together with the 6 piglets of Group 2 which were negative for pseudorabies antigens and antibodies. 14 days later, the 6 piglets of Group 1 were drawn back, and again, the 6 piglets of Group 3, which were negative for pseudorabies antigens and antibodies, were raised together with the 6 piglets of Group 2, and so on. After 4 serial passages, all the drawn piglets were killed in order to observe if there are any pathological changes.

It showed in the results that no abnormal changes were found during the clinical observation and gross anatomy of 30 experimental piglets infected with PRV-ZJ01-R strain, 30 experimental piglets infected with HeN1-R strain, and 30 experimental piglets infected with JS-2012-R strain by the 4th serial passage of the cohabitation infection experiment, indicating that there was no reversion of virulence of the three attenuated strains. Therefore, the safety of the vaccines can be ensured since the viruses, after being inoculated into piglets, would not evolve into virulent viruses which are able to cause disease.

4. Genes Sequences Analysis

The genome amplification of the cultures of the $1^{st}$ passage to $110^{th}$ passage of PRV-ZJ01-R strain was accomplished by means of RT-PCR (The genomic DNA of the culture of different passages was amplified respectively). The product acquired from amplification was recovered, purified, and linked to the plasmid vector for sequencing, so that the nucleotide sequence of the viral gene was determined and transformed through computer software into the amino acid sequence of the virus. The obtained amino acids sequence was compared with the amino acids sequence of the parent virulent strain, i.e. PRV-ZJ01 strain via software for sequence analysis, and the amino acids sequence of the virus was characterized.

The genome amplification of the cultures of the $1^{st}$ passage to $110^{th}$ passage of PRV HeN1-R strain was accomplished by means of RT-PCR (The genomic DNA of the cultures of different passages was amplified respectively). The product acquired from amplification was recovered, purified, and linked to the plasmid vector for sequencing, so that the nucleotide sequence of the viral gene was determined and transformed through computer software into the amino acid sequence of the virus. The obtained amino acids sequence was compared with the amino acids sequence of the parent virulent strain, i.e. PRV HeN1 strain via software for sequence analysis, and the amino acids sequence of the virus was characterized.

The genome amplification of the cultures of the $1^{st}$ passage to $110^{th}$ passage of PRV JS-2012-R strain was accomplished by means of RT-PCR (The genomic DNA of the culture of different passages was amplified respectively). The product acquired from amplification was recovered, purified, and linked to the plasmid vector for sequencing, so that the nucleotide sequence of the viral gene was determined and transformed through computer software into the amino acids sequence of the virus. The obtained amino acids sequence was compared with the amino acids sequence of the parent virulent strain, i.e. PRV JS-2012 strain via software for sequence analysis, and the amino acids sequence of the virus was characterized.

It showed in the results that for the cultures of the $1^{st}$ passage to $110^{th}$ passage of PRV PRV-ZJ01-R strain, the amino acids encoded by each viral genes commonly have continuous deficiency of gI/gE/11K/28K genes, 3455 bp in total, of which the deficiency site and size are totally the same as those of PRV HN1201-R strain; for the cultures of the $1^{st}$ passage to $110^{th}$ passage of PRV HeN1-R strain, the amino acids encoded by each viral genes commonly have continuous deficiency of gI/gE/11K/28K genes, 3455 bp in total, of which the deficiency site and size are totally the same as those of PRV HN1201-R strain; for the cultures of the $1^{st}$ passage to $110^{th}$ passage of PRV JS-2012-R strain, the amino acids encoded by each viral genes commonly have continuous deficiency of gI/gE/11K/28K genes, 3455 bp in total, of which the deficiency site and size are totally the same as those of PRV HN1201-R strain; compared with their parent virulent strains, each of PRV PRV-ZJ01-R strain, PRV HeN1-R strain and PRV JS-2012-R strain has continuous deficiency of gI/gE/11K/28K genes, 3455 bp in total.

It indicated that a common characteristic change of the amino acids encoded by the viral genes of the different passages of cultures of PRV PRV-ZJ01-R strain, PRV HeN1-R strain and PRV JS-2012-R strain is consistent with that of the amino acids encoded by the viral genes of PRV HN1201-R strain, which is caused by the deficiency of genes encoding said amino acids sequences, showing the stability of the method of attenuating the PRV by passage according to the present invention, and in the meanwhile, further indicating that continuous deficiency of gI/gE/11K/28K genes, 3455 bp in total, in PRV is the reason for the reduction of virulence of its parent virulent strain.

Example 14: Preparation of the Attenuated Live Vaccines of PRV PRV-ZJ01-R Strain, PRV HeN1-R Strain and PRV JS-2012-R Strain The attenuated live vaccines of PRV PRV-ZJ01-R strain, PRV HeN1-R strain and PRV JS-2012-R strain were prepared according to the procedure in Example 3. The specific ratios of contents of the vaccines are shown in Table 17.

TABLE 17 ratios of contents of the attenuated live vaccines of PRV PRV-ZJ01-R strain, HeN1-R strain and JS-2012-R strain

| | Antigen ($TCID_{50}$) | Cryoprotectant (V/V) |
|---|---|---|
| Vaccine 6 (PRV-ZJ01-R strain) | $10^{6.0}$ | 50% |
| Vaccine 7 (HeN1-R strain) | $10^{6.0}$ | 50% |
| Vaccine 8 (JS-2012-R strain) | $10^{6.0}$ | 50% |

Example 15: Immunogenicity Assay of the Attenuated Live Vaccines of PRV PRV-ZJ01-R Strain, PRV HeN1-R Strain and PRV JS-2012-R Strain 30 9-day-old piglets which were negative for PRV antigens and PRV antibodies were randomly divided into 6 groups, each with 5 piglets, and the piglets were immunized with the attenuated live vaccines of PRV PRV-ZJ01-R strain, PRV HeN1-R strain and PRV JS-2012-R strain prepared in Example 3. Piglets in Group 1 were immunized with Vaccine 6, those in Group 3 were immunized with Vaccine 7 and those in Group 5 were immunized with Vaccine 8, and Groups 2, 4 and 6 were all the control groups. On day 21 after immunization, the piglets in Groups 1 and 2 were challenged with $1\times10^{7.0}$ $TCID_{50}$/piglet of PRV PRV-ZJ01 strain, those in Groups 3 and 4 were challenged with $1\times10^{7.0}$ $TCID_{50}$/piglet of PRV HeN1 strain, and those in Groups 5 and 6 were challenged with $1\times10^{7.0}$ $TCID_{50}$/piglet of PRV JS-2012 strain. After challenge, the body temperature of piglets was measured daily, and in the meanwhile clinical signs and death status were observed. The results are shown in Table 18.

TABLE 18

Results of immunogenicity assay of three attenuated live vaccines

| Group | Number of piglets | Dose of Challenge | Clinical signs and death status | Rate of protection |
|---|---|---|---|---|
| Vaccine 6 | 5 | $10^{7.0}TCID_{50}$/piglet of PRV-ZJ01 strain | Normal body temperature, normal appetite, no abnormal clinical signs, survived | 100% (5/5) |

TABLE 18-continued

Results of immunogenicity assay of three attenuated live vaccines

| Group | Number of piglets | Dose of Challenge | Clinical signs and death status | Rate of protection |
|---|---|---|---|---|
| Control group | 5 | $10^{7.0}$TCID$_{50}$/piglet of PRV-ZJ01 strain | All the pigs displayed symptoms like increased body temperature, depression, complete or partial loss of appetite, and significant clinical signs; two died on day 4 after challenge, and all died within 5 days after challenge. | 0% (0/5) |
| Vaccine 7 | 5 | $10^{7.0}$TCID$_{50}$/piglet of HeN1 strain | Normal body temperature, normal appetite, no abnormal clinical signs, survived | 100% (5/5) |
| Control group | 5 | $10^{7.0}$TCID$_{50}$/piglet of HeN1 strain | All the pigs displayed symptoms like increased body temperature, depression, complete or partial loss of appetite, and significant clinical signs; two died on day 4after challenge, and all died within 5 days after challenge. | 0% (0/5) |
| Vaccine 8 | 5 | $10^{7.0}$TCID$_{50}$/piglet of JS-2012 strain | Normal body temperature, normal appetite, no abnormal clinical signs, survived | 100% (5/5) |
| Control group | 5 | $10^{7.0}$TCID$_{50}$/piglet of JS-2012 strain | All the pigs displayed symptoms like increased body temperature, depression, complete or partial loss of appetite, and significant clinical signs; two died on day 4 after challenge, and all died within 5 days after challenge. | 0% (0/5) |

The results indicated that immunizing piglets with the attenuated live vaccines of PRV-ZJ01-R strain prepared in example 14 can block virus infection (i.e. prevent occurrence of clinical signs), and provide 100% (5/5) protection rate for piglets, while all the piglets in the blank control group died by day 5 after challenge; immunizing piglets with the attenuated live vaccine of PRV HeN1-R strain prepared in example 14 can block virus infection (i.e. prevent occurrence of clinical signs), and provide 100% (5/5) protection rate for piglets, while all the piglets in the blank control group died by day 5 after challenge; immunizing piglets with the attenuated live vaccine of PRV JS-2012-R strain prepared in example 14 can block virus infection (i.e. prevent occurrence of clinical signs), and provide 100% (5/5) protection rate for piglets, while all the piglets in the blank control group died by day 5 after challenge.

It has proven that the attenuated live vaccines of PRV PRV-ZJ01-R strain, PRV HeN1-R strain and PRV JS-2012-R strain can provide excellent protection, showing excellent immune protection and safety; meanwhile it indicated again that continuous deficiency of gI/gE/11K/28K genes, 3455 bp in total, from the PRV virus would have no effect on its immunogenicity.

Example 16: Broad-Spectrum Immunogenicity Assay of the Attenuated Live Vaccine of PRV HN1201-R Strain 50 9-day-old piglets which were negative for PRV antigens and PRV antibodies were randomly divided into 10 groups, each with 5 piglets, and the piglets were immunized with the attenuated live vaccine of PRV HN1201-R strain prepared in Example 3. Piglets in Groups 1, 3, 5, 7 and 9 were immunized with Vaccine 1, and Groups 2, 4, 6, 8 and 10 were the control groups. On day 21 after immunization, the piglets in Groups 1 and 2 were challenged with $1\times10^{7.0}$ TCID$_{50}$/piglet of PRV HN1202 strain, those in Groups 3 and 4 were challenged with $1\times10^{7.0}$ TCID$_{50}$/piglet of PRV Fa strain, those in Groups 5 and 6 were challenged with $1\times10^{7.0}$ TCID$_{50}$/piglet of PRV PRV-ZJ01 strain, those in Groups 7 and 8 were challenged with $1\times10^{7.0}$ TCID$_{50}$/piglet of PRV HeN1 strain, and those in Groups 9 and 10 were challenged with $1\times10^{7.0}$ TCID$_{50}$/piglet of PRV JS-2012 strain. After challenge, the body temperature of piglets was measured daily, and in the meanwhile clinical signs and death status were observed. The specific results are shown in Table 19.

TABLE 19

Results of broad-spectrum immunogenicity assay of the attenuated live vaccines of PRV HN1201-R

| Group | Number of piglets | Dose of Challenge | Clinical signs and death status | Rate of protection |
|---|---|---|---|---|
| 1 | 5 | $10^{7.0}$TCID$_{50}$/piglet of HN1202 strain | Normal body temperature, normal appetite, no abnormal clinical signs, survived | 100% (5/5) |
| 2 | 5 | $10^{7.0}$TCID$_{50}$/piglet of HN1202 strain | All the pigs displayed symptoms like increased body temperature, depression, complete or partial loss of appetite, and significant clinical signs; Four died on day 4 after challenge, and all died within 5 days after challenge. | 0% (0/5) |
| 3 | 5 | $10^{7.0}$TCID$_{50}$/piglet of Fa strain | Normal body temperature, normal appetite, no abnormal clinical signs, survived | 100% (5/5) |
| 4 | 5 | $10^{7.0}$CID$_{50}$/piglet of Fa strain | All the pigs displayed symptoms like increased body temperature, depression, complete or partial loss of appetite, and significant clinical signs; two died on day 4 after challenge, and all died within 5 days after challenge. | 0% (0/5) |
| 5 | 5 | $10^{7.0}$CID$_{50}$/piglet of PRV-ZJ01 strain | Normal body temperature, normal appetite, no abnormal clinical signs, survived | 100% (5/5) |

TABLE 19-continued

Results of broad-spectrum immunogenicity assay of the attenuated live vaccines of PRV HN1201-R

| Group | Number of piglets | Dose of Challenge | Clinical signs and death status | Rate of protection |
|---|---|---|---|---|
| 6 | 5 | $10^{7.0}$CID$_{50}$/piglet of PRV-ZJ01 strain | All the pigs displayed symptoms like increased body temperature, depression, complete or partial loss of appetite, and significant clinical signs; two died on day 4 after challenge, and all died within 5 days after challenge. | 0% (0/5) |
| 7 | 5 | $10^{7.0}$CID$_{50}$/piglet of HeN1 strain | Normal body temperature, normal appetite, no abnormal clinical signs, survived | 100% (5/5) |
| 8 | 5 | $10^{7.0}$CID$_{50}$/piglet of HeN1 strain | All the pigs displayed symptoms like increased body temperature, depression, complete or partial loss of appetite, and significant clinical signs; two died on day 4 after challenge, and all died within 5 days after challenge. | 0% (0/5) |
| 9 | 5 | $10^{7.0}$TCID$_{50}$/piglet of JS-2012 strain | Normal body temperature, normal appetite, no abnormal clinical signs, survived | 100% (5/5) |
| 10 | 5 | $10^{7.0}$TCID$_{50}$/piglet of JS-2012 strain | All the pigs displayed symptoms like increased body temperature, depression, complete or partial loss of appetite, and significant clinical signs; two died on day 4 after challenge, and all died within 5 days after challenge. | 0% (0/5) |

The results indicated that immunizing piglets with the attenuated live vaccine of PRV HN1201-R strain prepared in Example 3 can block virus infection (i.e. prevent occurrence of clinical signs), and provide 100% (5/5) protection rate for piglets, while all the piglets in the blank control group died by day 5 after challenge.

It has proven that the attenuated live vaccine of PRV HN1201-R strain prepared according to the present invention can provide a fully protection against the epidemic PRV from different sources, showing excellent broad-spectrum immunogenicity.

Those are only preferred embodiments of the present invention as described above, which cannot be used to limit the present invention in any forms. Although the present invention has been revealed as described above in the form of the preferred embodiments, they are not intended to limit the present invention. Any skilled in the art can make several changes to the above technical content or modify the above technical content as equivalent embodiments with equivalent substitution, without departing from the technical scope of the present invention. Any simple change, equivalent substitution or modification etc, which are made to the above embodiments, based on the technical nature of the present invention, without departing from the content of technical solution of the present invention, should fall within the scope of protection of the present invention.

The invention claimed is:

1. An attenuated strain of the porcine pseudorabies virus obtained by using a method of attenuating the porcine pseudorabies virus, wherein said attenuated strain of the porcine pseudorabies virus does not express gI, gE, 11K and 28K proteins, wherein the genes of said attenuated strain of porcine pseudorabies virus have a serial deletion of 3455 bp starting from the 890$^{th}$ nucleotide of gI gene, and wherein the method of attenuating porcine pseudorabies virus comprises:

(1) a step of cultivating the pseudorabies virus adapted to cell culture, wherein the pseudorabies virus is inoculated into subcultured mammalian cells, and then subcultured for at least five passages so as to obtain the porcine pseudorabies virus strain adapted to the subcultured mammalian cells; and (2) a step of attenuating the porcine pseudorabies virus, the porcine pseudorabies virus strain adapted to the subcultured mammalian cells are inoculated into subcultured avian cells and then subcultured for at least one passage so as to obtain the attenuated strain of the porcine pseudorabies virus.

2. The attenuated strain of the porcine pseudorabies virus as described in claim 1, wherein said attenuated strain of porcine pseudorabies virus is PRV HN1201-R strain, wherein said PRV HN1201-R strain is deposited in the China Center for Type Culture Collection on Mar. 17, 2015, of which the accession number is CCTCC NO. V201516 and the address of depositary is Wuhan University, Wuhan, China.

3. A vaccine composition comprising:

a carrier; and an attenuated strain of the porcine pseudorabies virus as described in claim 1 or a culture thereof, wherein a content of said attenuated strain of the porcine pseudorabies virus is at least $10^{6.0}$ $TCID_{50}$/piglet.

4. The vaccine composition as described in claim 3, further comprising antigen of porcine circovirus.

5. The vaccine composition according to claim 3, wherein the content of said attenuated strain of the porcine pseudorabies virus is in the range of $10^{6.0}$ $TCID_{50}$/piglet-$10^{7.0}$ $TCID_{50}$/piglet.

* * * * *